United States Patent
Vallejo et al.

(10) Patent No.: US 10,933,244 B2
(45) Date of Patent: Mar. 2, 2021

(54) SYSTEM AND METHOD OF PAIN RELIEF BASED ON FREQUENCY BASED ANALYSIS OF TEMPORAL NOCICEPTIVE SIGNALS

(71) Applicants: Ricardo Vallejo, Bloomington, IL (US); David Leonardo Cedeno, Normal, IL (US); William J. Smith, Bloomington, IL (US)

(72) Inventors: Ricardo Vallejo, Bloomington, IL (US); David Leonardo Cedeno, Normal, IL (US); William J. Smith, Bloomington, IL (US)

(73) Assignee: LUMBRERA LLC, Bloomington, IL (US)

( * ) Notice: Subject to any disclaimer, the term of this patent is extended or adjusted under 35 U.S.C. 154(b) by 234 days.

(21) Appl. No.: 15/860,117

(22) Filed: Jan. 2, 2018

(65) Prior Publication Data
US 2018/0185645 A1    Jul. 5, 2018

Related U.S. Application Data

(60) Provisional application No. 62/539,756, filed on Aug. 1, 2017, provisional application No. 62/440,547, filed on Dec. 30, 2016.

(51) Int. Cl.
*A61N 1/36* (2006.01)
*A61B 5/00* (2006.01)
*A61B 5/048* (2006.01)
*A61B 5/04* (2006.01)
(Continued)

(52) U.S. Cl.
CPC ...... *A61N 1/36071* (2013.01); *A61B 5/04001* (2013.01); *A61B 5/048* (2013.01); *A61B 5/04017* (2013.01); *A61B 5/4047* (2013.01); *A61B 5/4824* (2013.01); *A61B 5/4836* (2013.01); *A61N 1/0556* (2013.01); *A61N 1/36139* (2013.01); *A61N 1/36171* (2013.01); *A61N 1/37264* (2013.01)

(58) Field of Classification Search
CPC .............. A61N 1/36071; A61N 1/0556; A61N 1/36139; A61N 1/36171; A61N 1/37264; A61B 5/04001; A61B 5/04017; A61B 5/048; A61B 5/4047; A61B 5/4824; A61B 5/4836
USPC .......................................... 607/46
See application file for complete search history.

(56) References Cited

U.S. PATENT DOCUMENTS

2008/0208284 A1    8/2008  Rezai et al.
2015/0321003 A1*  11/2015  Pless .................... A61N 5/0622
                                                            600/9

(Continued)

*Primary Examiner* — Christopher A Flory
*Assistant Examiner* — Minh Duc G Pham
(74) *Attorney, Agent, or Firm* — Burns & Levinson LLP; Bruce D. Jobse

(57) ABSTRACT

An apparatus, system and technique selectively eliminates the noxious signal components in a neuronal signal by creating an interfering electrical signal that is tuned to a given frequency corresponding to the oscillatory pattern of the noxious signal, resulting in a modified neuronal signal that substantially reproduces a normal, no-pain neuronal signal. The disclosed system and technique of pain relief is based on the hypothesis that the temporal profile of pain signals encodes particular components that oscillate at unique and quantifiable frequencies, which are responsible for pain processing in the brain.

22 Claims, 24 Drawing Sheets

(51) Int. Cl.
*A61N 1/372* (2006.01)
*A61N 1/05* (2006.01)

(56) References Cited

U.S. PATENT DOCUMENTS

2016/0175594 A1* 6/2016 Min .................. A61N 1/36171
607/62
2016/0271413 A1 9/2016 Vallejo et al.

* cited by examiner

SYSTEM AND METHOD OF PAIN RELIEF BASED ON FREQUENCY BASED ANALYSIS OF TEMPORAL NOCICEPTIVE SIGNALS

BACKGROUND

Living things are equipped with sensing units that are constantly probing the environment in order to react and adapt to it. In animals, the neuron is the basic sensing unit, and specialized neurons have evolved to provide the organism with variable capabilities that allow it to capture images, sounds, temperature, pressure (i.e. touch), and other inputs from the environment. Organisms have evolved to respond to these external stimuli, depending on their specific needs for survival, which is dependent on their physical abilities. Many of the reactions by the organism to external stimuli are conditioned by a natural need to protect itself from any external dangers. The process of nociception has evolved within the nervous system to allow an organism to respond to certain stimuli that is harmful or potentially harmful. In mammals, specialized neurons play the role of nociceptors and are directly involved in the processing of pain. The sensation of pain is a necessary component of a reflex nociceptive system that allows the organism to react to harmful environmental events. However, when pain becomes aberrant and chronic, it will develop in a pathological condition that requires medical interventions.

Currently, chronic pain is considered a pathology and many available therapies attempt to ameliorate this condition. From an etiological perspective, chronic pain may be of nociceptive, inflammatory, or neuropathic origin. In nociceptive pain, peripheral nociceptors become activated and react to external stimuli (touch, temperature) at thresholds that are well below what a person can tolerate under a normal nociceptive reflex. Inflammatory pain is associated with processes that involve certain molecular entities (receptors, neurotransmitters, cytokines, etc.) involved in inflammation, which may exacerbate nociceptive pathways. Neuropathic pain is primarily associated with nerve injury, which results in an unbalanced and sensitized nervous system.

Regardless of its etiology, chronic pain signals are transmitted via ascending pathways from the periphery to the brain via the spinal cord. A pain signal involves the conduction of an action potential along the axons of nociceptive neurons in the affected body structures. The action potential then activates the release of neurotransmitters in the synapse between two neurons at the dorsal root ganglion. Synaptic neurotransmission carries the nociceptive signal to neurons located in the dorsal horn of the spinal cord, which then sends this signal to the thalamus for further processing in the brain. It is generally accepted that dysfunction of neural tissue results in persistent changes in the function of the nervous system, which then manifests as chronic pain.

Both unmyelinated C-fibers and myelinated Aδ-fibers contain a variety of nociceptors with specific functionality depending on the level and characteristics of the stimuli. These are usually classified as chemoreceptors, mechanoreceptors, and thermal receptors, with some of them being polymodal while also operating for sensing at different stimulus thresholds. For example, skin is innervated by C-fibers and Aδ-fibers with nociceptors that respond distinctively different to cold temperatures. C-fiber nociceptors are involved with the dull pain felt when skin is exposed to cold temperatures above freezing, while Aδ-fiber nociceptors predominantly contribute to pricking pain felt below freezing temperatures. Furthermore, in vivo studies, as described in a publication by Cain, Khasabov, and Simone entitled *Response properties of mechanoreceptors and nociceptors in mouse glabrous skin: an in vivo study. J Neurophysiol.* 2001 April; 85(4):1561-74, have demonstrated that the response of C-fiber nociceptors to heat and cold is dependent on the intensity of the stimulus. The intensity of the stimulus (increase in temperature for heat, or decrease in temperature for cold) influences the firing frequency of a C-fiber nociceptor as illustrated in FIGS. 1A and 1B. Similarly, mechanoreceptors in Aβ fibers respond differently to force (i.e. pressure over area), as illustrated in FIG. 1C.

FIGS. 1A to 1C illustrate that the stimulus is encoded in the nociceptive signal as a specific temporal profile, in which the number of action potentials fired increases with the strength of the impulse. Recordings of action potentials can be performed in vivo in human peripheral nociceptors through a technique known as microneurography. Many of the studies utilizing microneurography evaluate the latency of nerve fiber responses. The latency is defined as the time elapsed between two action potentials and is equivalent then to the period of a cyclic signal. A publication by Serra, Bostock, Solà, et al. entitled *Microneurographic identification of spontaneous activity in C-nociceptors in neuropathic pain states in humans and rats. Pain.* 2011 153: 42-55, shows that changes in latency underlie the differences in neuron response to varying noxious and non-noxious stimuli. These changes in latency, or period in repeating signals, directly correlate to changes in the frequencies of the firing of action potential comprising the signal, demonstrating that nociceptive signals induced by noxious stimuli are characterized by a frequency pattern that is distinctively different than signals induced by non-noxious stimuli.

A publication by Dose and Taccola entitled *Two distinct stimulus frequencies delivered simultaneously at low intensity generate robust locomotor patterns. Neuromodulation.* 2016 August; 19(6):563-75, demonstrated similar behavior in motor neurons. These authors show that locomotor patterns from single motor neurons are composed of complex temporal profiles that encode information, which is required for locomotion. A frequency-based power analysis of the complex temporal signals reveal that four distinct frequencies (8, 11, 35, and 172 Hz) are involved in the locomotive response, and that removal of these components from the temporal signal deteriorates locomotion. Interestingly, synthetic trains of signals that contain these four frequencies reproduce the complex natural signal and a synthetic composition that resembles the natural one. Furthermore, a train that combines two of the frequencies (35 and 172 Hz) reproduces the effects of the train with four frequencies or the natural signal.

Accordingly, a need exists for an apparatus, system and technique which is capable of identifying the oscillatory patterns of noxious components in a neuronal signal and for neutralizing the noxious components.

A further need exists for an apparatus, system and technique which is capable of generating an interfering electrical signal tuned to the oscillatory pattern of the noxious signal frequency components in a neuronal signal, resulting in a modified neuronal signal that resembles the non-stimulated state neuronal signal.

A further need exists for an apparatus, system and technique for selectively modulating a noxious neuronal signal by creating an interfering electrical pulse that is tuned to a given frequency corresponding to the oscillatory pattern of a noxious signal, resulting in a modified neuronal signal that substantially reproduces a normal, no-pain neuronal signal.

SUMMARY

Disclosed is an apparatus, system and technique for selectively modulating a noxious neuronal signal by creating an interfering electrical signal that is tuned to a given frequency corresponding to the oscillatory pattern of the noxious signal, resulting in a modified neuronal signal that substantially reproduces a normal, no-pain neuronal signal. The disclosed system and technique of pain relief is based on the hypothesis that the temporal profile of pain signals encodes particular components that oscillate at unique and quantifiable frequencies, which are responsible for pain processing in the brain. In other words, during a no-pain state the brain receives a complex signal from the pain pathway that is coded in such a way that the temporal profile of a particular combination of frequencies is interpreted as no-pain.

A signal-compensating device delivers an electrical signal that provides pain relief based on the analysis of nociceptive signals in the afferent pathway. This signal may be delivered for a particular subject based on feedback that has been previously generated from individuals suffering a particular pain condition (i.e. nociceptive, inflammatory, neuropathic), and/or from computational models of peripheral or central nociceptive pathways (neurons). The signal generated by the device relies on the pathologic condition of the subject and the analysis of both the temporal profile of the nociceptive signal and the frequency profile, resulting from the temporal profile of the nociceptive signal being transformed into the frequency domain using suitable time domain to frequency domain transform methods, such as Fourier transforms or others.

In embodiments, the acquired temporal signal may be compared to a control signal obtained from any of a database of individuals with no pain, computational models, the same patient's pathways that are not associated with pain, and/or when the pain has been relieved temporarily by using medication or other means to alleviate pain. The signal compensating device compares the acquired temporal signal with the control signal, e.g. signals obtained with pain, and identifies whether key frequency components are missing or extraneous relative to the no-pain state. The device then will modify the acquired signal causing either the missing frequency components to be added or causing additional frequency components to be cancelled so that a signal that more closely resembles the control signal, i.e. a no-pain signal. Furthermore, the system is able to distinguish if the pain signal is of nociceptive (thermal, mechanic, chemical origin), inflammatory or neuropathic as the temporal signals will be encoded according to its origin based on the identify characteristics of the signal.

In embodiments, the etiology of a pain signal is diagnosed and the system, based on the diagnosis, generates a compensation signal. Data describing a plurality of nociceptive signals has been previously stored in a memory module associated with the device. The acquired nociceptive signal is matched by the device to one of the nociceptive control signals in memory, and, based on the characteristics of the matched nociceptive control signal, the signal compensating device produces a signal that compensates the subject's nociceptive signal, as described in detail further.

According to one aspect of the disclosure, a method for neutralizing pain-inducing components in a nociceptive signal in an afferent pathway comprises: A) acquiring a nociceptive signal at a sensing point in an afferent pathway, the nociceptive signal having a temporal profile; B) performing a time domain to frequency domain transformation of the temporal profile to create a first frequency based power analysis identifying corresponding frequency components of the acquired nociceptive signal; C) comparing the first frequency based power analysis with a second frequency based power analysis of a comparison control signal having a temporal profile; D) identifying at least one frequency component not common between the first frequency based power analysis and the second frequency based power analysis; and E) generating a correction signal which when combined with the nociceptive signal results in a modified nociceptive signal having a temporal profile substantially similar to the temporal profile of the comparison control signal. In embodiments, the method further comprises: F) applying the modulation signal to the afferent pathway distal of the sensing point in the afferent pathway. In embodiments, D) may comprise identifying absent or extraneous frequency component in the first frequency based power analysis compared to the second frequency based power analysis. In embodiments, E) may comprise generating a modulation signal which when applied to the afferent pathway causes the missing frequency component to be substantially present, or the extraneous frequency component to be absent, in the nociceptive signal distal of the sensing point.

According to another aspect of the disclosure, an electromagnetic stimulation system comprises: a memory for storing a plurality of modulation signal parameter programs; a selection device for selecting one of the plurality of modulation signal parameter programs, a signal generator controllable by a selected of the plurality of modulation signal parameter programs; and an output unit for connection to at least one electrode; wherein the stimulation system is configured to provide a modulation signal generated by the signal generator in accordance with a selected of the modulation signal parameter programs to the at least one electrode via the output unit, and wherein the electrode is configured for applying the modulation signal at an application point in an afferent pathway of a mammalian subject causing a nociceptive signal substantially distal of the application point to have a temporal profile which is different from a temporal profile of a nociceptive signal substantially proximal of the application point.

According to yet another aspect of the disclosure, an electromagnetic stimulation system comprises: memory for storing a plurality of temporal profiles of pain signals; an input section receptive to a signal acquired at a sensing point in an afferent pathway of a subject, the signal acquired having a temporal profile; an output unit for connection to at least one electrode; and a processing module configured to: compare and determine if a match exists between a temporal profile of the acquired signal and one of the plurality of temporal profiles of pain signals in memory; perform a time domain to frequency domain transformation of a temporal profile of a pain signal matching the signal acquired to create a first frequency based power analysis identifying corresponding frequency components of the signal acquired; compare the first frequency based power analysis with a second frequency based power analysis of a comparison signal having a temporal profile; identify at least one frequency component not common between the first frequency based power analysis and the second first frequency based power analysis; and generate a modulation signal which when combined with the signal acquired at the sensing point results in a modified signal having a temporal profile substantially similar to the temporal profile of the comparison signal.

According to still another aspect of the disclosure, a method for neutralizing components in a signal in a neurological pathway of a mammalian subject, the method comprises: A) acquiring a signal at a sensing point in the neurological pathway of the subject, the signal having a temporal profile; B) identifying a characteristic in a frequency based power analysis of the signal acquired; and C) generating a correction signal which when applied to the neurological pathway combines with the signal acquired resulting in a modified signal absent the identified characteristic. In embodiments, the method further comprises D) applying the correction signal to the neurological pathway. In embodiments, B) may comprise identifying absent or extraneous frequency component in the first frequency based power analysis compared to the second frequency based power analysis. In embodiments, B) may further comprise generating a modulation signal which when applied to the afferent pathway causes the missing frequency component to be substantially present, or the extraneous frequency component to be absent, in the nociceptive signal distal of the sensing point.

DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

The system and methods described herein will embody many potential forms and techniques for implantation of a system capable of relieving pain associated with various chronic pain states (e.g. nociceptive, inflammatory, neuropathic pain, or combination thereof). The specific design of the system described herein is a guideline for understanding the system, but it will be obvious to the skilled in the art that it shall not limit the range of its description.

Figure 1A:
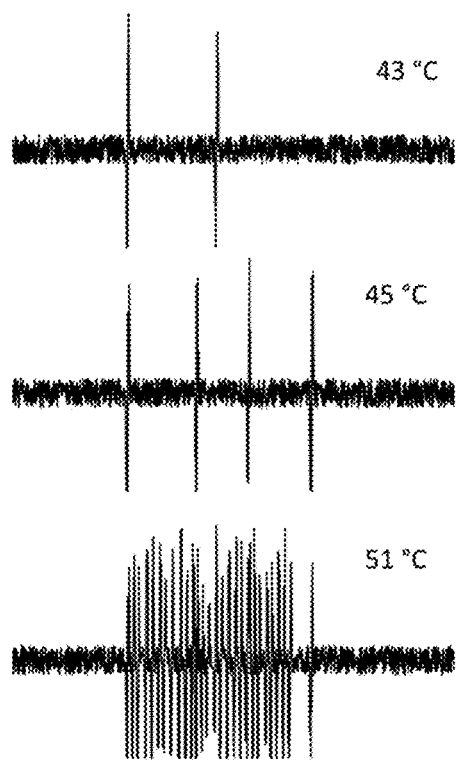
FIG. 1A is a conceptual illustration of evoked responses of a C-fiber nociceptor as a function of an increase in the temperature of a heat stimulus.
Figure 1B:
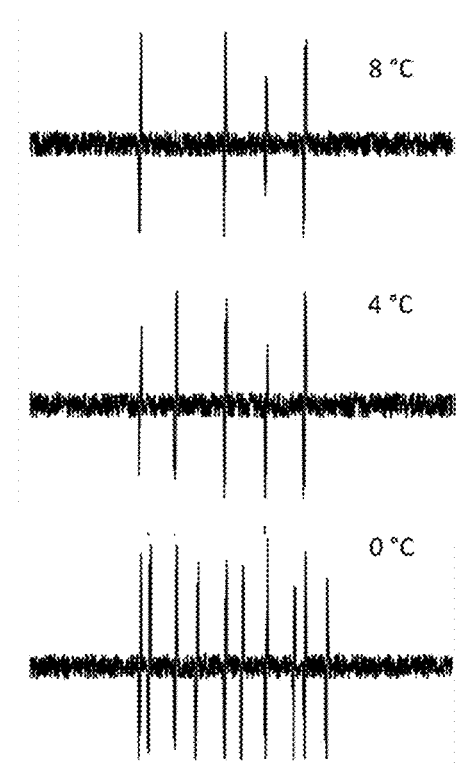
FIG. 1B is a conceptual illustration of evoked responses of a C-fiber nociceptor as a function of a decrease in the temperature of a cold stimulus.
Figure 1C:
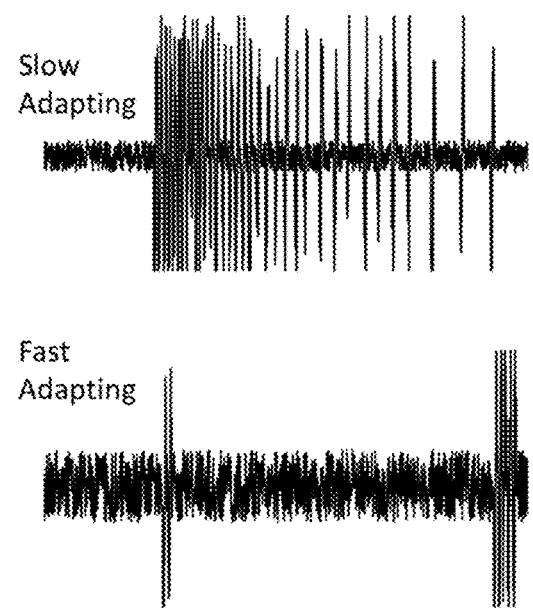
FIG. 1C is a conceptual illustration of evoked responses of an Aβ mechanoreceptor to a constant force for a given period of time (FIG. 1C).
Figure 2A:
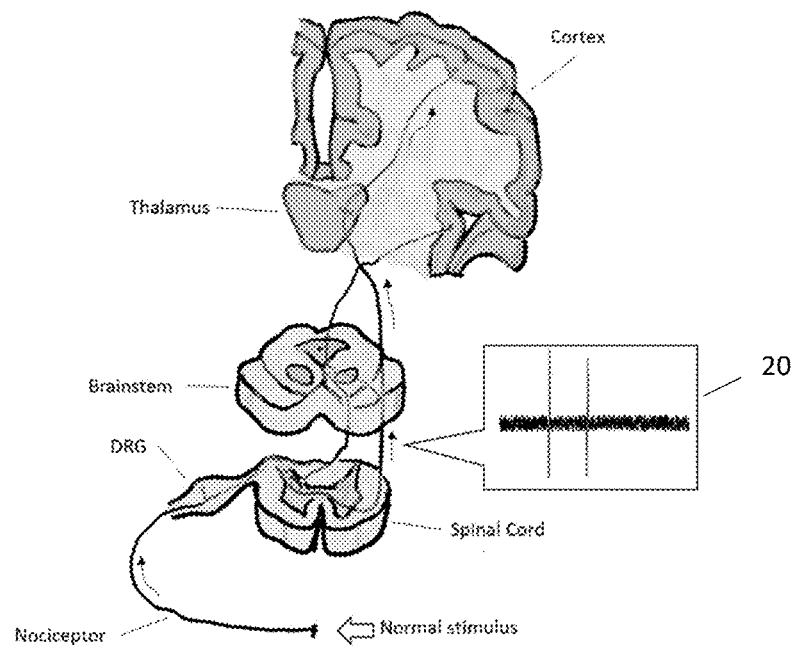
FIG. 2A illustrates conceptually a nociceptive ascending pathway in the case of a normal stimulus that does not induce a pain sensation, in accordance with the disclosure.
Figure 2B:
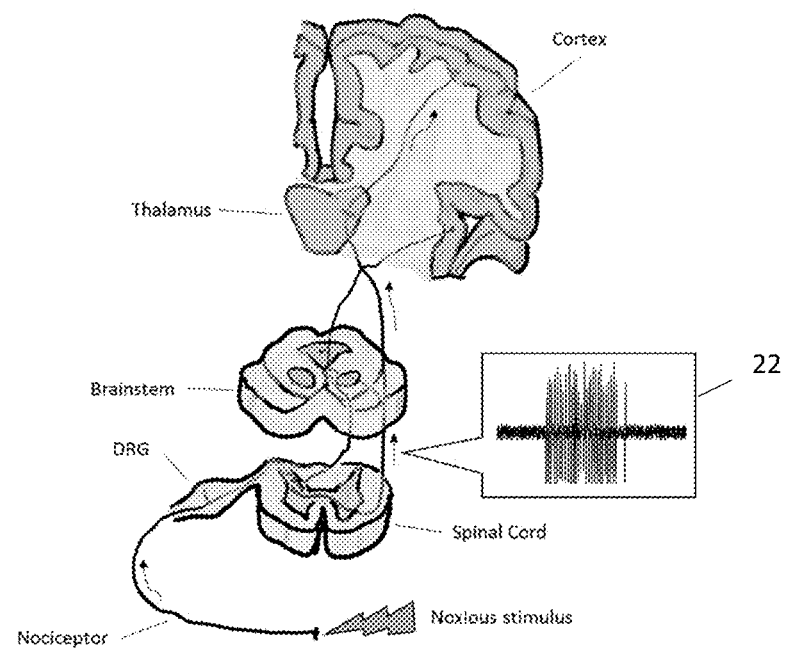
FIG. 2B illustrates conceptually a nociceptive ascending pathway in the case of a noxious stimulus that induces a pain sensation, in accordance with the disclosure.

The disclosed system and technique of pain relief is based on the hypothesis that the temporal profile of pain signals encodes particular components that oscillate at unique and quantifiable rates and are composed of particular frequencies, which are responsible for pain processing in the brain. In other words, during a no-pain state the brain receives a complex signal from the pain pathway that is coded in such a way that the temporal profile of a particular combination of frequencies that is interpreted as no-pain. During a pain state, such signal is disrupted by either the presence or absence of certain frequency components that perturb the no-pain state signal and thus the brain processes the signal as pain. This hypothesis implies that nociceptive, inflammatory, and neuropathic pain may have distinctive components in the frequency domain, which are not distinguishable, if the signals are analyzed in the temporal domain. FIG. 2A-B are illustrations of the nociceptive ascending pathway. FIG. 2A illustrates the case of a normal stimulus that does not induce a pain sensation. A probe at the level of the spinal cord may record a distinctive signal as illustrated conceptually in the insert window, corresponding to a no-pain state. FIG. 2B illustrates the case of a noxious stimulus that induces a pain sensation. A probe at the level of the spinal cord may record a distinctive signal as illustrated conceptually in the insert window, corresponding to the pain state.

Figure 3A:
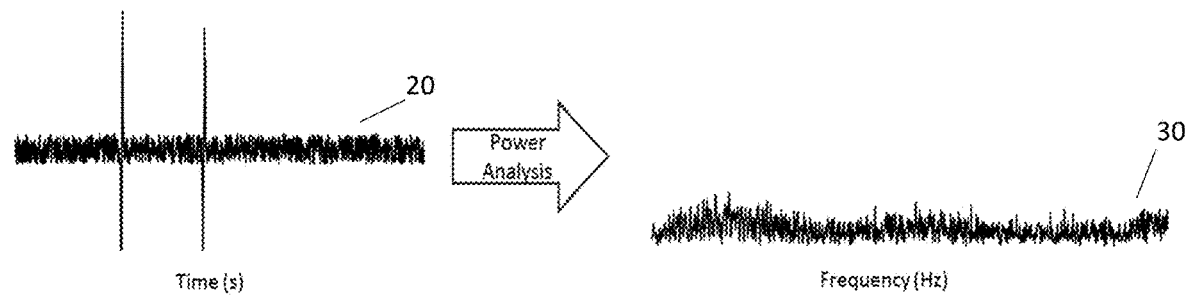
FIG. 3A-B are conceptual illustrations of the processing of a temporal signal corresponding to a no-pain state and a pain state, respectively, into a frequency-based spectrum after a power analysis, in accordance with the disclosure.
Figure 3B:
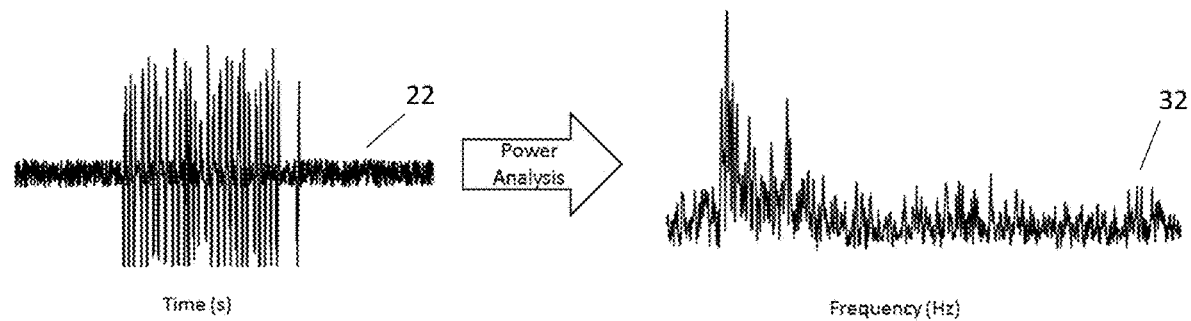

FIGS. 3A-B illustrate the frequency-based spectrums 30 and 32, representing no-pain state and a pain state, respectively, and after a power analysis processing of a no-pain state temporal signal 20 and a pain state temporal signal 22, respectively. Referring to FIG. 3A, in one embodiment, the system may record the temporal signal in the afferent pathway and analyze such signal and the components thereof in the frequency domain using suitable time domain to frequency domain transform methods, such as Fourier transforms or others. In embodiments, the acquired temporal signal 22 may be compared to a control signal 20 obtained from any of a memory or database of individuals with no pain, computational models, the same patient's pathways that are not associated with pain, and/or when the pain has been relieved temporarily by using medication or other means to alleviate pain. The signal compensating device compares the acquired temporal signal 22 with the control signal 20, e.g. a signal obtained with and/or without pain, and identifies whether key frequency components in their frequency profiles, 32 and 30, respectively, are missing or added relative to the no-pain state, as illustrated in FIGS. 3A and 3B. The signal compensating device then will compensate the acquired signal by causing the adding of the missing frequency components or cancelling of extraneous frequency components to achieve a signal that more closely resembles the control signal, i.e. a no-pain signal. Furthermore, the signal compensating device is able to distinguish if the pain signal is of nociceptive (thermal, mechanic, chemical origin), inflammatory or neuropathic as the temporal signals will be encoded according to its origin based on the identify characteristics of the signal.

In another embodiment, the etiology of a pain signal is diagnosed and the system, based on the diagnosis, generates a compensation signal. In this embodiment, data describing a plurality of nociceptive signals has been previously stored in a memory module associated with the device. The nociceptive signal is matched by the device to one of the nociceptive signals in the memory module and, based on the characteristics of the matched nociceptive signal, the device produces a signal that compensates the subject's nociceptive signal, as described in detail further.

In another embodiment, a signal generated by the device may be customized based on the patient's diagnosis. In this case, one or multiple signals with different frequencies, pulse widths, and or amplitudes may be programmed to activate one or multiple electrical contacts positioned in proximity to the targeted structure (cutaneous, subcutaneous, peripheral nerve, dorsal root ganglion, epidural, dorsal horn, dorsal columns, specific locations of the spinal cord, thalamic structures, cortical structures) based on the data store of nociceptive signals already described.

Systems Components

Figure 4:
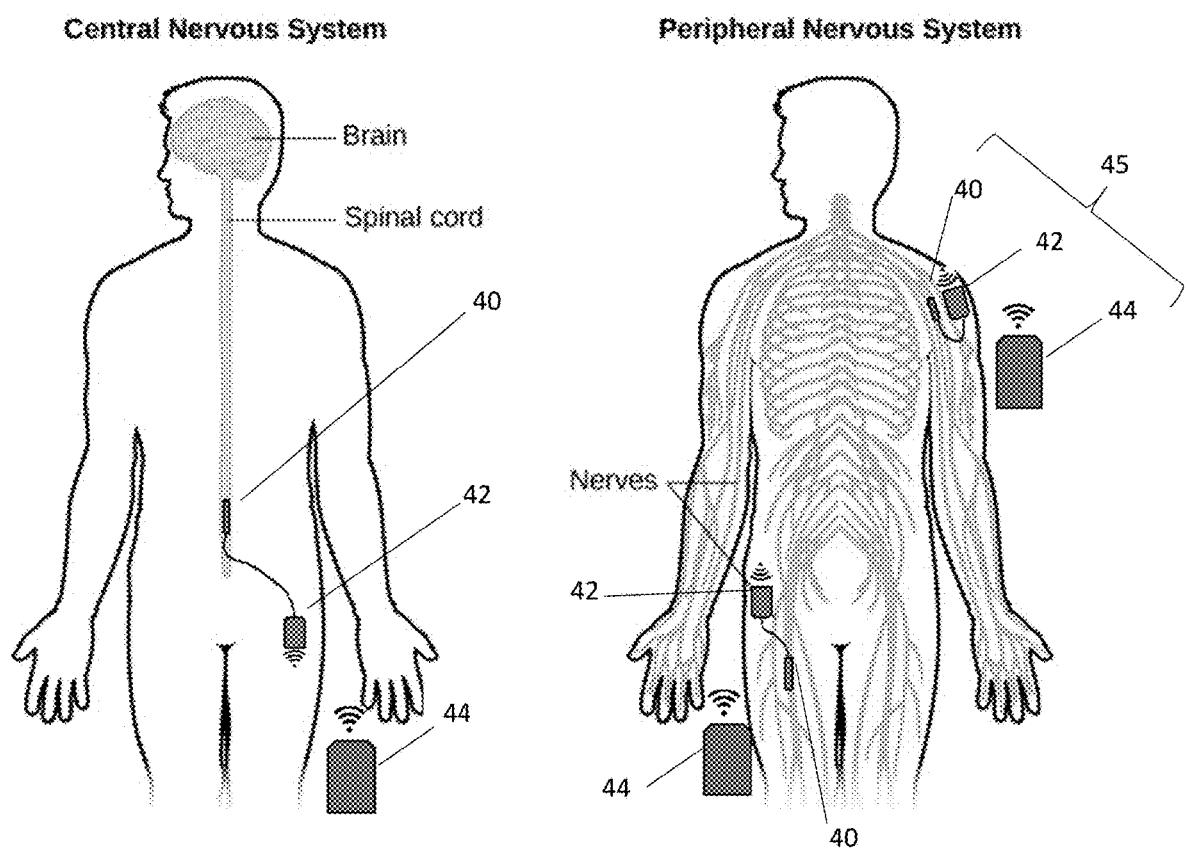
FIG. 4 illustrates conceptually implantation locations of system, both in the central nervous system through a spinal cord implantation and in the peripheral nervous system through major peripheral nerves, such as the sciatic and brachial, in accordance with the disclosure.

FIG. 4 illustrates conceptually embodiments of a system 45 that may be utilized to perform the methods disclosed herein. In embodiments, as illustrated in FIG. 4, the system 45 comprises electrical leads 40 containing an array of electrodes, device 42 and optional remote control 44. Any of the functions described herein may be located within any of the elements 40, 42 and 44.

Figure 12:
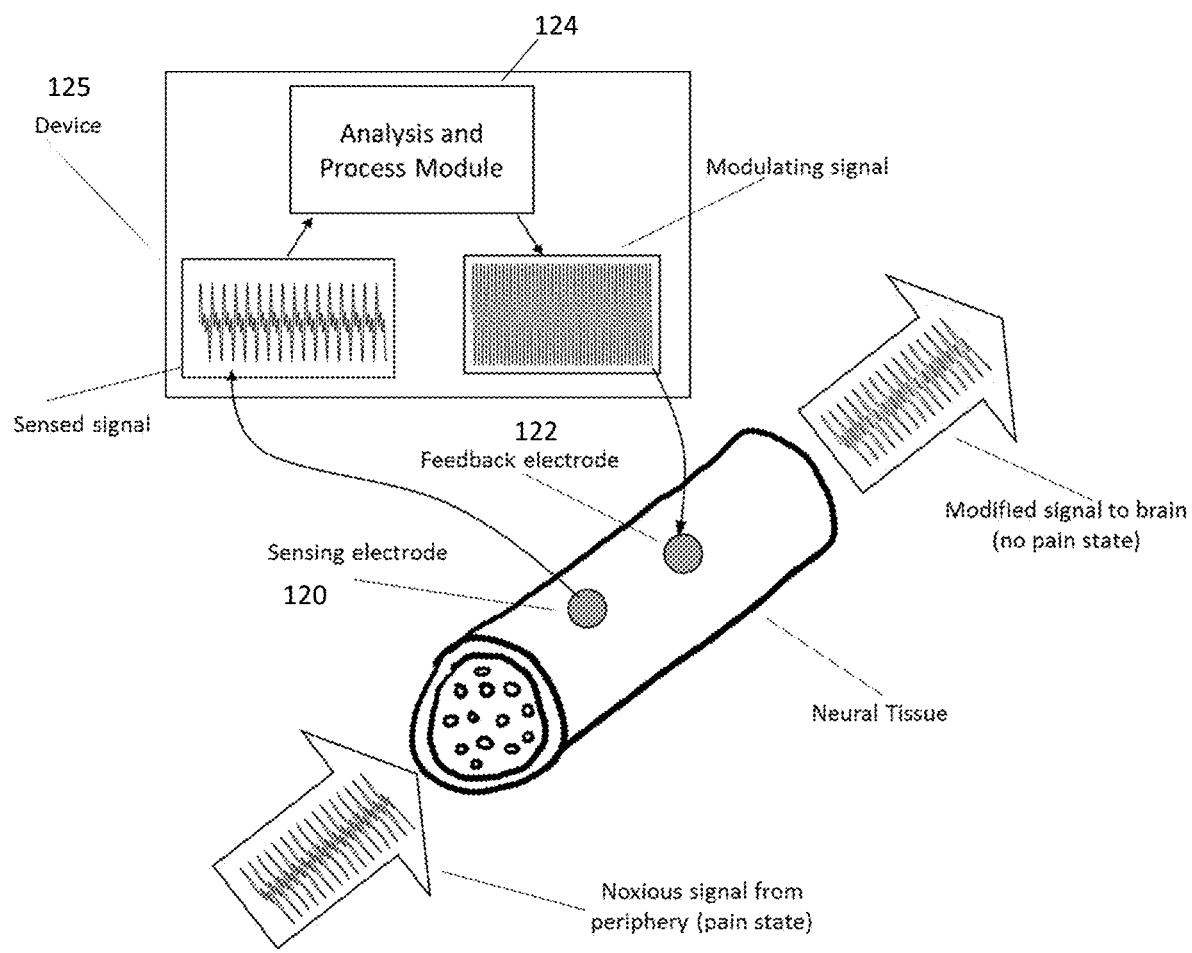
FIG. 12 is a conceptual illustration of a system for correcting a noxious neural signal using a signal generated from power analysis and comparison with reference signal to generate a signal that destructively interferes with frequency component correlated with noxious stimulus, in accordance with the disclosure.
Figure 13:
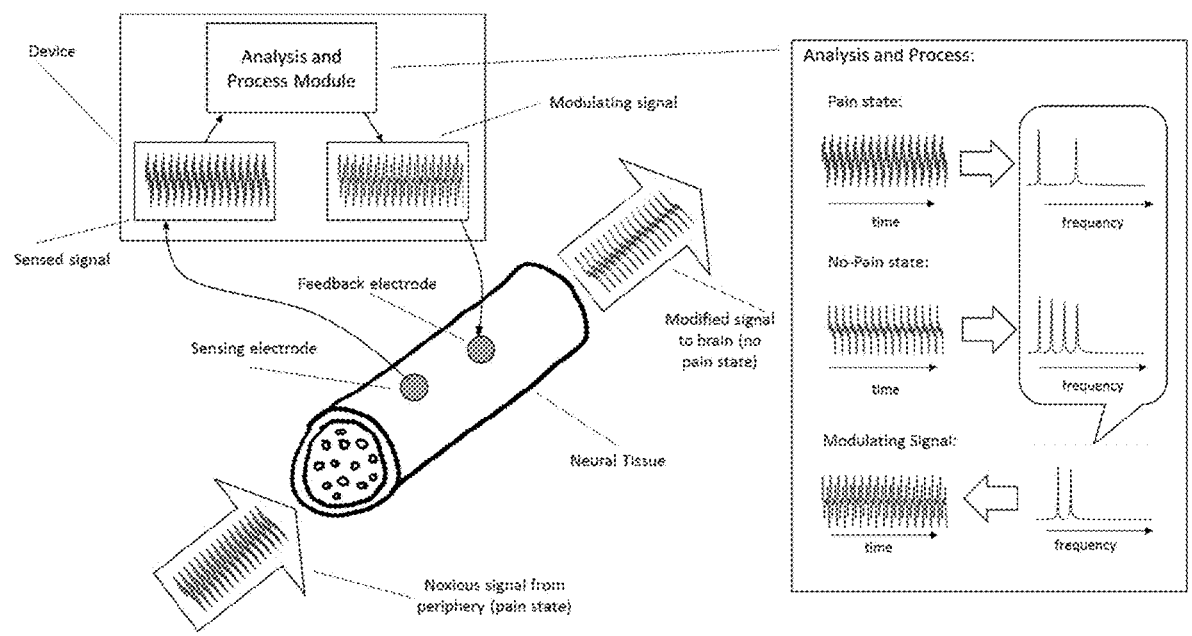
FIG. 13 is a conceptual Illustration of a system for modifying a noxious neural signal using a signal generated by comparing the power spectra of a pain and a no-pain signal, the modulating signal adding frequency components, which are absent in the pain signal, in accordance with the disclosure.

Device 42 may be may be hermetically sealed in a housing made of a durable biocompatible material, such as stainless steel or titanium, and has an output interface for establishing electrical connection with electrode(s) implemented within leads 40 that deliver the correction signals to glial cells and neurons and communicate with remote 44 through appropriate connectors. Device 42 is electrically coupled to electrical leads 40, each of which may be implemented with at least one or more electrode contacts. In an embodiment, a pair of leads is coupled to the device 42 using appropriate connectors, as illustrated in FIGS. 12-13. In another embodiment, a single lead implemented with an array of electrodes can be used.

Figure 11:
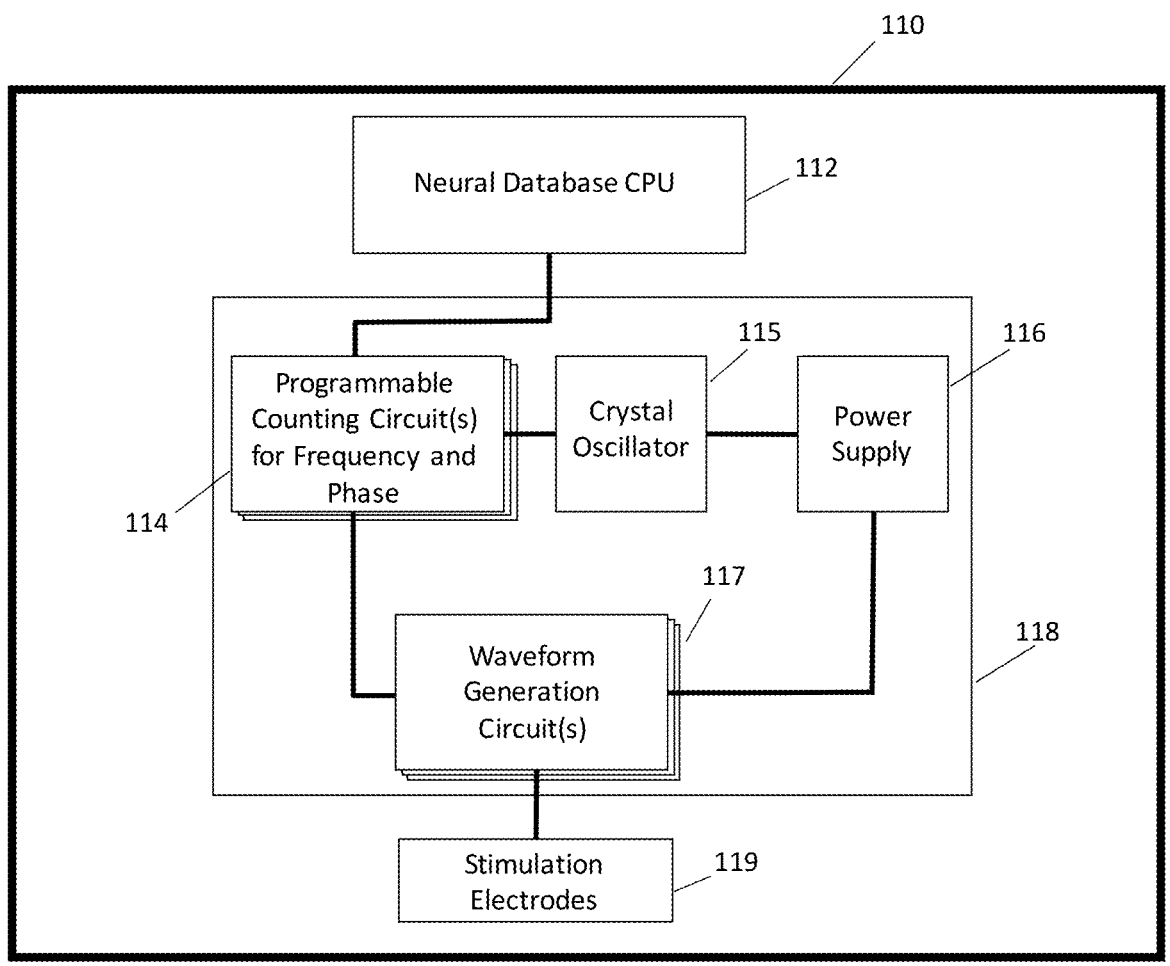
FIG. 11 is a conceptual illustration of a neurostimulation system showing the flow of information from the Neural Database and its utilization in creating the waveforms for stimulation, in accordance with the disclosure.

In one embodiment, device 42, may be implemented to include modules similar to modules 112 and 118 of FIG. 11, including with processing logic 112 associated with neural database/memory and a communication port for transmitting data to a remote platform 44 such, as a remote control, mobile device or remote computer, such as a transceiver, e.g.

a Bluetooth transceiver, a Bluetooth transmitter, a radio-frequency transceiver, a radio-frequency transmitter, a WiFi transceiver, and a WiFi transmitter, via a serial communication device pursuant to RS232 standard, Bluetooth, or other communications protocol. In embodiments, device 42 and processor module 112 may be implemented with any number of small, medium or large scale electrical processing or logic components, such as those described herein, and may be embodied with a small footprint. In embodiments, processor module may be implemented in an integrated circuit package and may comprise any of one or more microcontrollers, microprocessors, a programmable logic controller (PLC), a field programmable gate array (FPGA), or an application-specific integrated circuit (ASIC), collectively referred to hereafter as the processor. The central processing module 112 may be implemented with a microprocessor integrated circuit or may comprise reduced functionality small-scale logic, but, in either implementation includes a wireless transceiver functionality that enables bidirectional wireless communication of information with an external programmer unit (not shown) or a user-controlled remote 44. The neural database/memory associated with module 112, may be implemented with any combination either RAM or ROM memory, and is used to store a processing program, executable by central processing module 112, which generates functional information of the generator 20. The central processing module 25 is able to store and retrieve information from a memory module 28 as commanded by the user. The power source 116 may comprise a rechargeable battery and electronic circuitry that distributes power from the battery to all the other components in device 42.

A protocol may be provided for operating the accessory device in a low power mode and selectively initiating the processing logic to a higher-power state with increased data retention in relation to the acquired signal. The waveform generation module 117 may comprise electronic circuitry that allows the delivery of waveforms of any waveshape, including but not limited to biphasic or monophasic pulses, sinusoidal trains, sawtooth trains, triangle trains, and bursts thereof. In one embodiment, module 117 comprises electronic circuitry that allows the delivery of noise signals, such as white noise, with a constant power spectral density, or pink noise, with equal energy in octave intervals, or other noise signals in which the energy within the signal spectrum is distributed in other patterns. Module 117 is further capable of generating a range of interphase delays and is designed to deliver a signal, with amplitude which is either voltage controlled or current controlled, over a range of values. The signal generator module 23 is also able to generate pulses with a duty cycle. The module 117 is controlled by the module 112 according to parameters selected by the user in an external programmer unit (or control remote). Note, module 117 may be implemented with analog or digital circuitry or a combination thereof. In one embodiment, all or most of the functional elements of module 117 may be fabricated on a single integrated circuit chip including a processing logic and associated memory, and one or more digital oscillators. Alternatively, the digital oscillators may be replaced with wave tables having stored therein mathematical descriptions of various waveform data values which are convertible into analog signals using a digital to analog converter. Such wavetables may be stored in processor module/memory module 112. In embodiments the various modules of device 42 may communicate over a central bus internal thereto or may have dedicated direct connections therebetween, or any combination thereof.

In one embodiment, device 42 may be programmed by a clinician using software that allows control of all the aspects of the system 45. The software may be accessible in a computer-based interface called the Clinician Programmer (CP) software. The software may be implemented with wireless communication protocols for remote access of the device 42. The CP software enables the clinician to communicate with module 112 and 118 to define a set of parameters, e.g. any of amplitude, frequency, phase, phase polarity, waveform shape, and width (rectangular waveform), etc., of the signal generated by module 117. Such defined parameter sets may be stored as one or more configuration programs in memory associated with remote 44 and transmittable to device 42 via telemetry logic for control of module 117. The CP software may enable the clinician to further define which parameter the patient my control with the remote controller 36 and to define any limits on such parameter.

FIG. 4 illustrates conceptually implantation locations of system 45, both in the central nervous system through a spinal cord implantation and in the peripheral nervous system through major peripheral nerves, such as the sciatic and brachial. In embodiments, the system 45 comprises electrical leads or cuffs 40 containing an array of electrodes, device 42 and optional remote control 44. The leads 40 are placed surgically or percutaneously in the epidural or subdural space of the cervical, lumbar or thoracic spinal cord of a patient, as illustrated in FIG. 4. Such placement may be accomplished by laying the patient prone and placing a pillow or some form of support under the abdomen to decrease lordosis of the lumbar spine. Insertion and placement of the leads 40 at other anatomical locations may require other patient positioning, or surgical approach. The final placement of the leads 40 is achieved with assistance of fluoroscopic or other imaging technique guidance. The leads 40 are connected to the signal-compensating device 42, which may be implanted in an appropriate area of the body or positioned outside the body. Lead 40 may be connected to device 42 via wireless transmission protocols. In still other embodiments, the signal-compensating device 42 may be implanted in an appropriate area of the body or worn outside the body and communicate wirelessly with a user remote control 44 which communicates wirelessly with signal-compensating device 42.

The electrical leads 40 may be placed surgically or percutaneously, using fluoroscopic, ultrasound or other imaging technique guidance, in the proximity of the DRG or intraspinal nerve roots. In embodiments, the leads 40 and/or device 42 may be placed in the proximity of the peripheral nervous system for nerves extending to the limbs, including the sciatic and femoral nerves or any of its branches in the lower limb and the brachial nerve or any of its branches in the upper limb, as illustrated in FIG. 4. In order to localize the nerves, several imaging guiding techniques, including, but not limited to, ultrasound, fluoroscopy, magnetic resonance images, computer tomography, electromyography, etc. Alternatively, sympathetic or parasympathetic fibers may be stimulated to control other conditions included, but not limited to headaches and migraines (occipital nerves), facial pain (facial nerves, sphenopalatine ganglion, trigeminal nerves), complex regional pain syndrome (stellate ganglion, lumbar sympathetic nerves, etc.), abdominal pain (splanchnic nerves, celiac plexus, superior hypogastric ganglion, impar ganglion), These methods can be extended for other peripheral nerves in the body.

Figure 5:
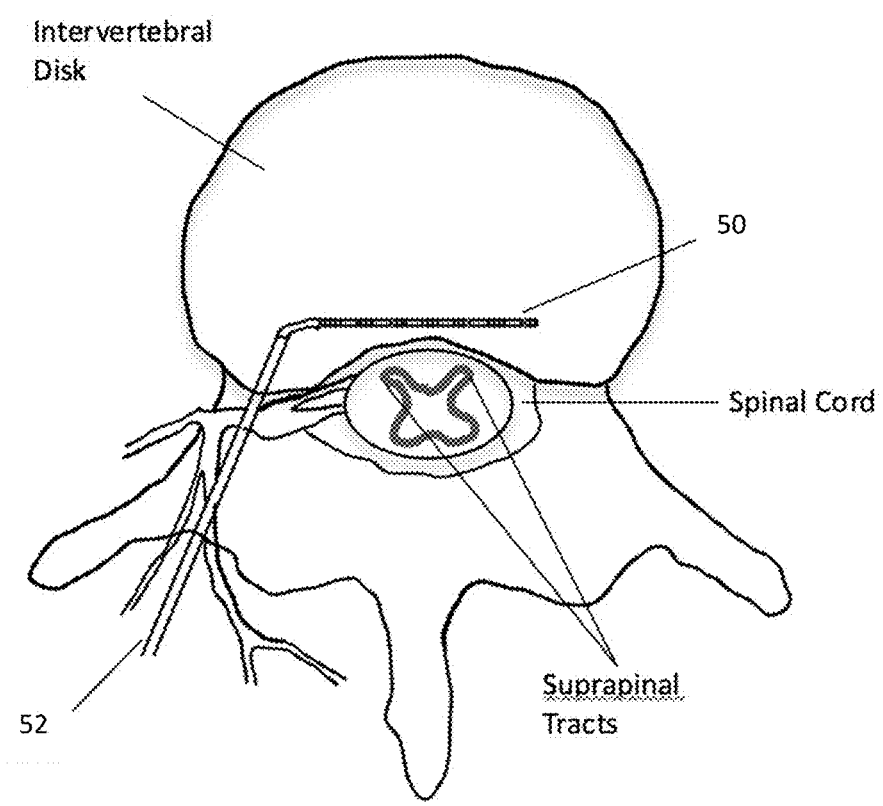
FIG. 5 illustrates conceptually implantation location of a stimulation lead in the intervertebral disk for stimulation of the afferent supraspinal tract, with stimulation the lead and its curved introducer for implantation of the lead through the superior articular process and into the disk, in accordance with the disclosure.

In embodiments, instead of lead 40, a stimulation lead 50 may be implanted in the intervertebral disk for stimulation of the afferent supraspinal tract, as illustrated in FIG. 5. A curved introducer may be utilized for implantation of the lead through the superior articular process and into the disk. The electrical stimulation lead 50 is inserted in the posterior side of an intervertebral disc in order to stimulate the spinal cord, herein called Transdiscal Spinal Cord Stimulation. Positioning of the stimulation lead 50 may be performed using the Seldinger technique, lateral to the superior articular process, advancing the lead posteriolaterally at mid-disk height. A uniquely designed curved tool 52 may be used to help clear a path for advancement of the lead, using the aforementioned Seldinger technique. A specially designed lead with a more rigid tip, able to advance through the annular portion of the disk may be utilized with this process. In embodiments, another lead is placed through the opposite superior articular process space and is used to pull the lead through for placement. The intradiscal lead may be placed in any of the intervertebral discs between vertebral levels T8 and L2, wherein the superior articular process space is large enough for access and the spinal cord remains intact prior to its split into the cauda equina. The placement of the lead 50 in the intradiscal location allows for stimulation of the supraspinal tract, where afferent fibers from the periphery travel to carry information to the brain. The placement of lead 50 is illustrated in FIG. 5.

According to another aspect of the disclosure, disclosed herein is a method for establishing a neuromodulation database and a system that utilizes the database for therapeutic purposes. The system described herein, referred to as a data driven neurostimulator is, in one embodiment, a fully integrated implantable system, which communicates with a memory module that stores a neuromodulation database in order to deliver condition specific therapeutic electrical stimulations via a lead or cuff containing one or multiple electrodes. In one embodiment, the system will be capable of both stimulating the patient and recording a patient's neuronal signals to expand the database.

Figure 6:
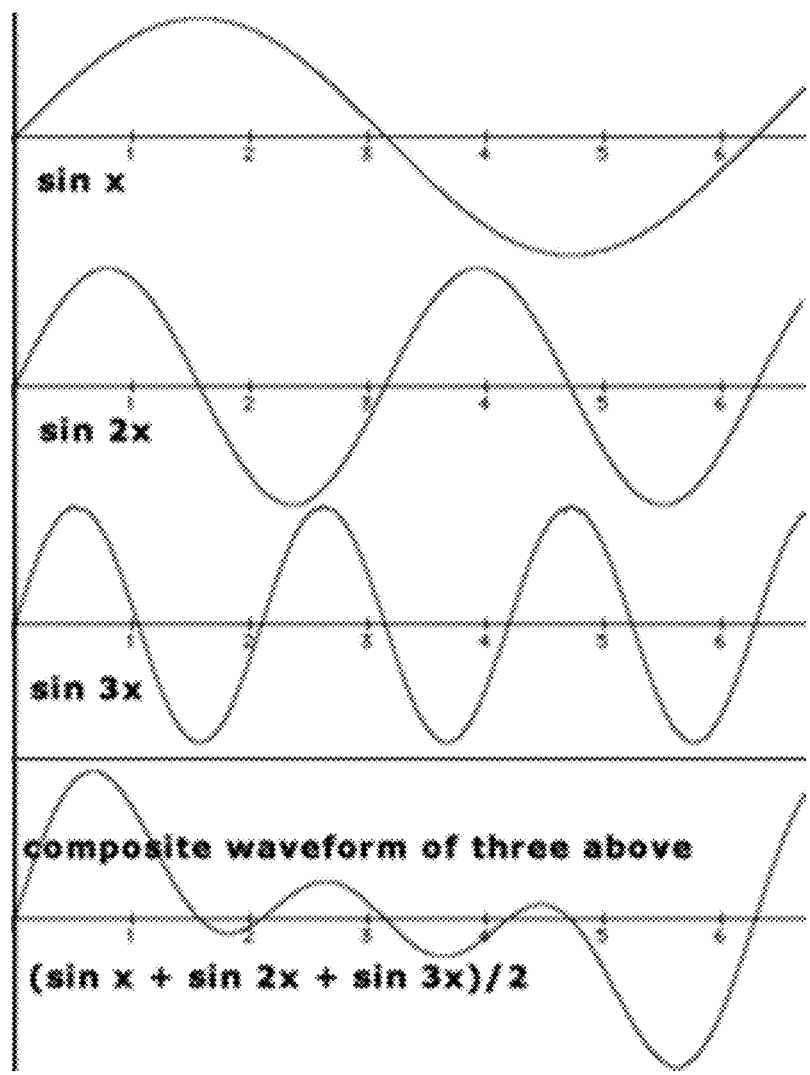
FIG. 6 is a conceptual illustration of simple sine waves of varying frequencies, which are added to create a complex composite periodic waveform.
Figure 7:
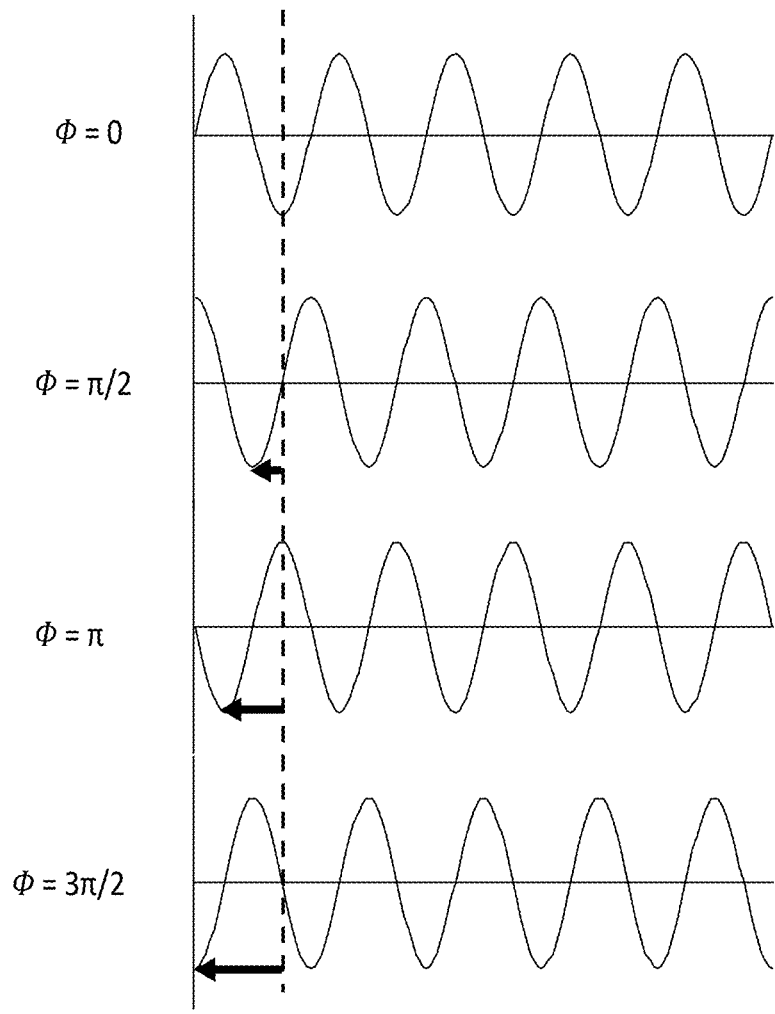
FIG. 7 is a conceptual illustration of a simple sine wave with varying phase, which is added to move a waveform horizontally through time.

Nociceptive signals are transmitted through the axons of neurons via electrical events called action potentials. When a stimulus acts on a nociceptor neuron, this causes physical chemical processes that result in the propagation of an electrophysiological signal. A system that can stop pain through alteration of specific frequency artifacts in the action potentials fired by nociceptive neurons during a pain state is described here. It is possible to describe some of the technical aspects of the system by modeling the axons of neurons as if they were conducting wires. For example, when a function generator set to produce a sinusoidal voltage waveform is connected to a conducting wire, the wire will experience a periodic buildup and deficit of electrons therein. If a voltage probe is connected to the wire in order to analyze a fluctuation at a certain point, and the voltage is graphed over time, the probe will reproduce a characteristic sinusoidal wave modeled by the equation: sin (x). The buildup and deficit of electrons in the wire resembles the motion of ions such as $Na^-$, $Cl^-$, $K^+$, and $Ca^{2+}$ in and out of a neuron. Thus, a neuron can be modeled as a wire with a current induced by a stimulus being passed through it. In a nociceptive neuron, a noxious stimulus is transmitted along a neuron in a cyclic fashion oscillating at a particular characteristic frequency. In a typical nerve, a complex pattern of action potentials is created as a result of the superposition of the various individual action potentials of the individual neurons that are part of a nerve fiber. This process can be illustrated using the complex waveforms that is created through the addition of multiple different simple sinusoidal waves of different frequency. FIG. 6 illustrates conceptually simple sine waves of varying frequencies, which are added to create a complex composite periodic waveform. The individual simple waveforms can all be represented by the simple wave equation:

$$A*\sin(kx \pm ft)$$

where k and f control the phase (space) and frequency (time) characteristics of the wave. The variations in frequency (f) and amplitude (A) are illustrated in FIG. 6. When several different waves, with varying frequencies and phases, are added together a complex composite wave is formed that may appear to be irregular and even not periodic. FIG. 7 illustrates conceptually a simple sine wave with varying phase (k), which is added to move a waveform horizontally through time.

The complex composite waveform resulting from the addition of the simple waveforms in space and time is produced and characterized in the temporal domain, i.e. the waveform is described in terms of the variation of its amplitude as a function of time. This complex composite signal can be, however, analyzed as a weighted average of the frequencies and phases of the component signals of which it is comprised. This analysis can be carried out in what is known as the frequency domain. The analysis of a temporal signal into its frequency domain is possible using a mathematical operation, such as a Fourier transform, although other time to frequency transform operations may be used. Such operation allows for a complex temporal signal to be broken down into frequency components for analysis in a process known as deconvolution. This view of a waveform is known as the power analysis of a temporal signal in the frequency domain and allows for a more robust analysis of complex periodic signals.

In accordance with the present disclosure, neuronal signals can be modeled as electrical signals in wires, the principles used to modulate electrical signals in wires may be applied to neuronal signals. The use of circuitry components such as resistors, capacitors, and inductors, can be used to filter out an electrical signal in a wire based on the frequency components of the electrical signal. Such filters, which are known as high-pass and low-pass filters allow for signals oscillating at frequencies above or below a certain value to propagate along the wire. In some circuits this is governed mainly by a capacitor in the frequency-based filtering circuit. The capacitor determines a time constant for the circuit, which is characteristic of its capacitance. This governs how quickly or slowly a charge can be loaded or dissipated out of the circuit. When a low-pass and a high-pass filter are combined together in sequence, the results is known as a notch filter, which can selectively attenuate a specific frequency or frequency range.

Figure 8:
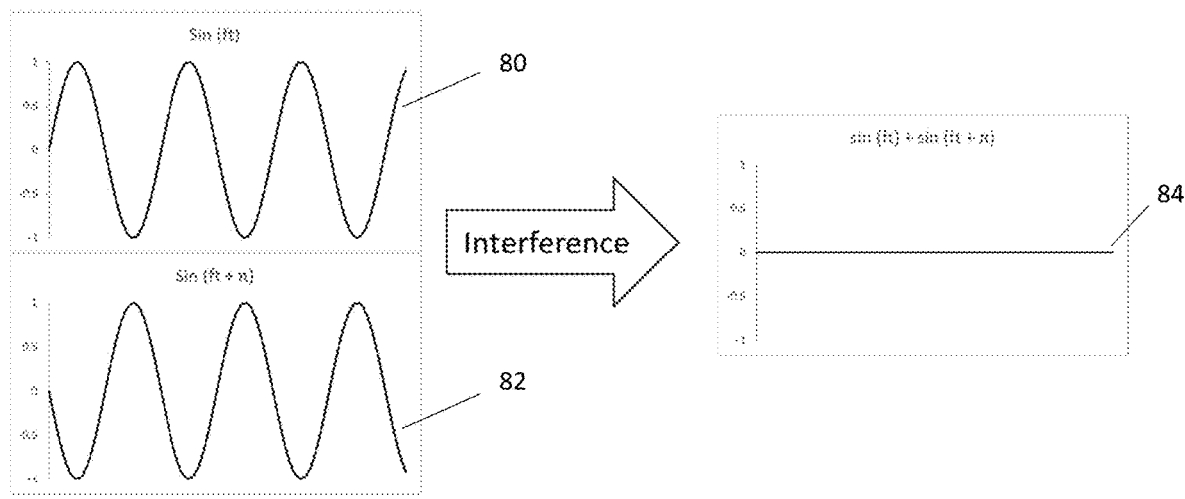
FIG. 8 is a conceptual illustration of the process of destructive interference in which a sin(ft) function is superimposed in time and space with another function of the same frequency, f, but phase shifted by Π radians, in accordance with the disclosure.

In addition to filtering, interference may be performed in electrical waves propagating along a wire. If the signal through the wire corresponds to a periodic increase and decrease of current flow in the material, then feeding a signal that has the same period of current flow (same frequency) and is delayed by half the period, e.g. 180° out of phase (phase shift, kx, of Π radians), will cancel out the signal. To understand this, imagine that at point x of the wire and time t, the electrons from the function generator are building up to their maximum capacity. If another function generator is used to create and provide a signal that oscillates at the same rate, and is delivered at the same time t, to point x, such that the flow of electrons is at the minimum capacity, then the lack of electrons will balance the increase of electrons, and the signal will be cancelled out. FIG. 8 is a conceptual illustration of the process of destructive interference in which a sin(ft) function 80 is superimposed in time and space with another function 82 of the same frequency, f, but phase shifted by Π radians, resulting in a negation of the function and the corresponding signal 84.

Figure 9A:
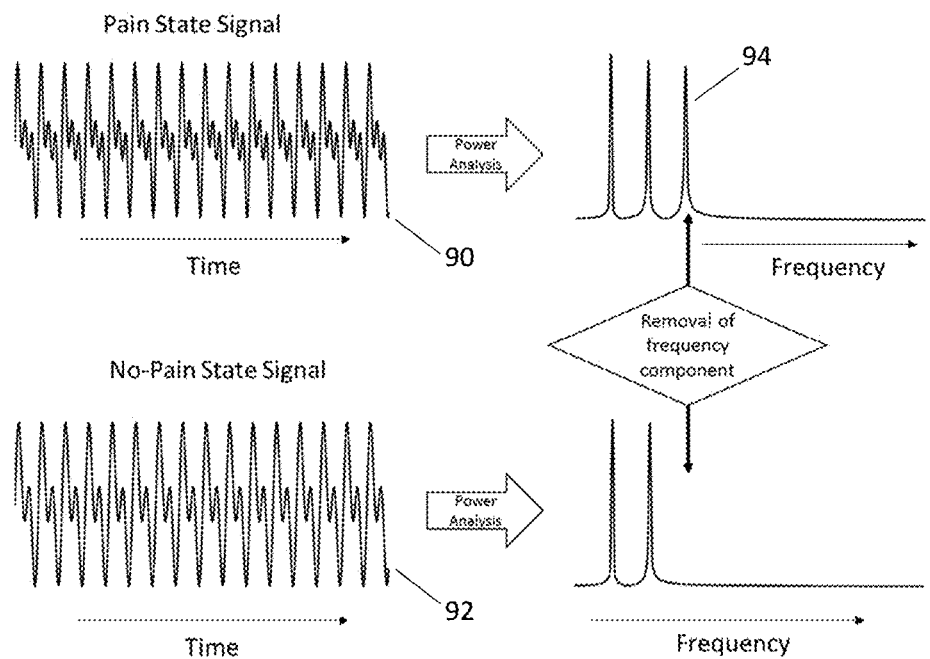
FIG. 9A-B are conceptual illustrations showing temporal and frequency domain differences between a hypothetical complex signal correlated to a pain state and a reference complex signal for the no-pain state, in accordance with the disclosure.
Figure 9B:
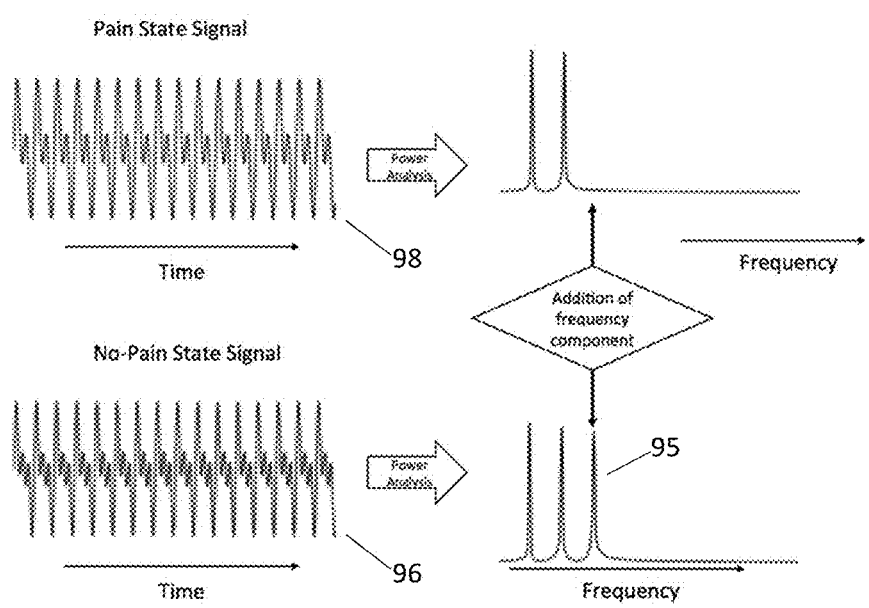

FIG. 9A-B are conceptual illustrations showing temporal and frequency domain differences between hypothetical complex signals correlated to a pain state and the reference complex signals for the no-pain state. FIG. 9A illustrates conceptually the case in which removal of a particular signal component 94 oscillating at a particular frequency (or frequencies) in the pain state signal 90 will render the no-pain state signal 92. In this scenario, either by destructive interference or frequency filtering, a complex signal made up of many frequencies can have one frequency removed, as illustrated in FIG. 9A. If it is desired to remove a particular component at frequency "F" from the complex signal, a notch filter or band reject filter can be placed to allow all signal frequencies through except for "F". Alternatively, a signal with frequency "F", but with a phase shift of Π, may be used to create destructive interference for frequency "F" only, allowing all of the remaining frequency components to pass. Both these methods would preserve the other frequencies in the complex signal 92. FIG. 9B illustrates the case in which addition of a particular signal component 95 oscillating at a particular frequency (or frequencies) to the pain state signal 98 will restore the no-pain state signal 96. Certain pain states may have nociceptive signals 98 in which certain frequency components 95 are absent, e.g. demyelinating neuropathy, painful diabetic neuropathy, etc., when compared to the no-pain state signal 96. In this case, the disclosed device will provide one or multiple signal components oscillating at a particular frequency or frequencies, which when added to the nociceptive signal will render the no-pain state signal 96, as illustrated conceptually in FIG. 9B.

In accordance with the present disclosure, the principles used in electrical wave modulation through a wire may be applied to a neuron propagating an action potential. In a neuronal signal, such as that related to pain or cyclic locomotive signals in muscles, the action potentials caused by the depolarization/repolarization due to ion flow through the axon membrane is similar to a complex sinusoidal waveform. Therefore, this signal can be acquired, analyzed and modified, as explained herein with reference to the Figures.

Figure 10:
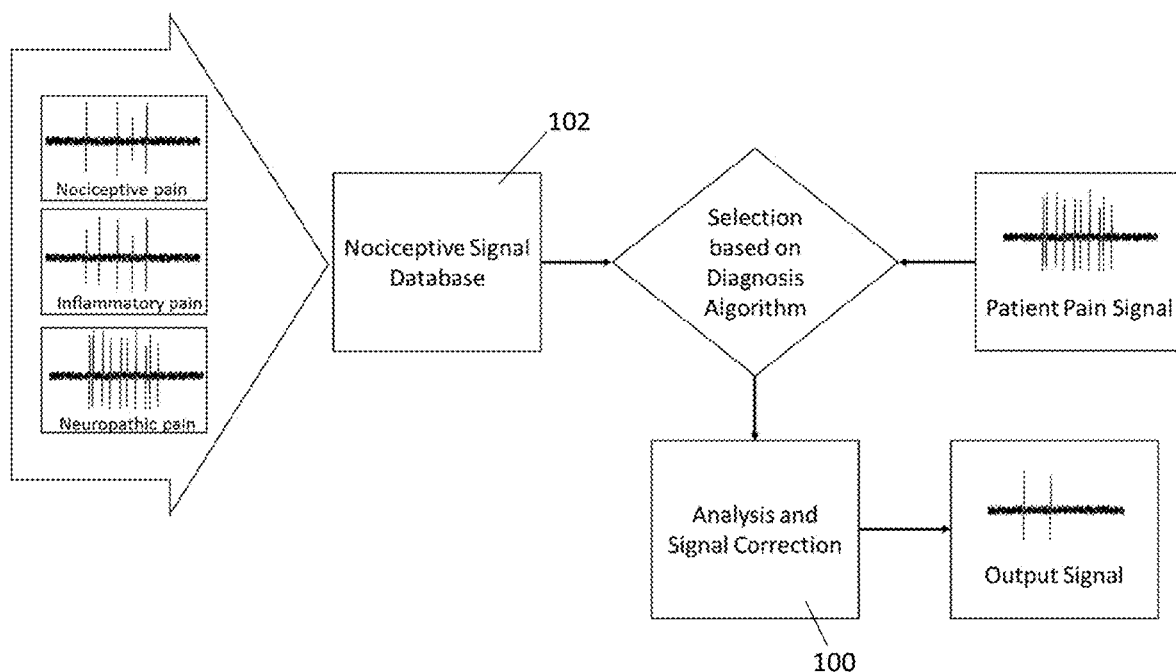
FIG. 10 is a flow chart illustrating conceptually the use of a database of nociceptive signals that guides the analysis and process of signal correction to produce a signal that corresponds to a no-pain state, in accordance with the disclosure.

FIG. 10 illustrates conceptually the process flow for using a database of nociceptive signals that guides the analysis and process of signal correction to produce a signal that corresponds to a no-pain state, as would be implemented with the system 110 of FIG. 11. The first step in this process is the characterization of the neuronal signal. It has been shown that very complex temporal locomotive signals from the ventral roots of rats show characteristic frequencies that dictate motion, when these are analyzed in the frequency domain via a power analysis. When the temporal components that corresponds to these frequencies are removed from the signal, locomotion ceases. In a similar way, a temporal nociceptive signal can be subjected to a power analysis and transformed into the frequency domain in order to first identify the frequency artifacts that characterize certain types of signals components that are processed in the brain as pain.

The system 110 comprises a memory module that stores a neuromodulation signal database 102 holding information on signal analysis across various pain pathologies represented as various programs and settings able to be accessed by the data driven analysis and signal correction module 100 of neurostimulator of system 110. The characterization of pain signals can be done in multiple ways. Either by type of pain, namely inflammatory, neuropathic, nociceptive, or mixed or by stimulus causing the pain, that is mechanical, thermal, or chemical, or by disease/pathology of the pain.

FIG. 11 is a conceptual illustration of a neurostimulation system 110 showing the interconnections of the neural database and processor 112 and signal compensation module 118 for creating waveforms transmittable to stimulation electrodes 119. The database and processor 112 in its simplest embodiment, comprises a simple set of integrated circuitry capable of storing floating point numbers corresponding to specific pain condition. The integrated circuit may be programmed on a device as simple as an Arduino board. The device may have stored variables for frequency and phase parameters for each pain state and is capable of basic arithmetic for the count calculations. The processor is also be capable of transmitting the parameters to a stimulator electrode device 119. This can be performed via Wi-Fi, Bluetooth, radiofrequency, or physical wiring. All of these functions can be programmed to a simple Arduino board, which makes clear to those skilled in the art, that a small integrated circuit device could be created to perform this function. In its more complicated embodiments, the processor is also able to perform the data analysis processes as described herein.

In an alternative embodiment, the analytical processes are performed in real time on the incoming neural signals by the implanted data driven neurostimulator. This embodiment encompasses a device that is adaptive and continually updates its output signal based on the signal it is receiving.

The signals stored in the neural database 112 or other data store may also be characterized by computational models in which neural elements, such as neural peripheral axons, dorsal root ganglions, dorsal horns, wide dynamic range neurons, dorsal columns, brain stem, or other neural structures involved in pain transmission, featuring realistic human fiber diameters and distributions, are modeled to predict the conduction patterns of pain and no-pain state signals.

The interaction between the neuromodulation database 112 and the data driven neurostimulator 118 can be implemented with various technologies. The database and processing logic 112 can be connected as a wearable small computational device, directly wired to the implantable data driven neurostimulator. In this embodiment the database and processing logic serves also as the programmer for the stimulator. In another embodiment, the database is wirelessly accessed or stored in the programmer and able to transmit waveform parameters to the data driven neurostimulator via Bluetooth, radiofrequency, Wi-Fi, or any other wireless data sharing connection.

FIG. 12 is a conceptual illustration of a system for correcting a noxious neural signal using a signal generated from power analysis and comparison with reference signal to generate a signal that destructively interferes with frequency component correlated with noxious stimulus. In FIG. 12, a signal acquired by sensing electrode 120 is provided to system 125 where the signal is analyzed and processed by module 124 and a modulating signal provided to feedback electrode 122.

FIG. 13 is a conceptual illustration of a system similar to system 125 of FIG. 12 for modifying a noxious neural signal using a signal generated by comparing the power spectra of a pain and a no-pain signal. The modulating signal provided to the feedback electrode adds frequency components which are absent in the pain signal, so that the modified signal transmitted to the brain is similar to a no-pain state signal.

Figure 14:
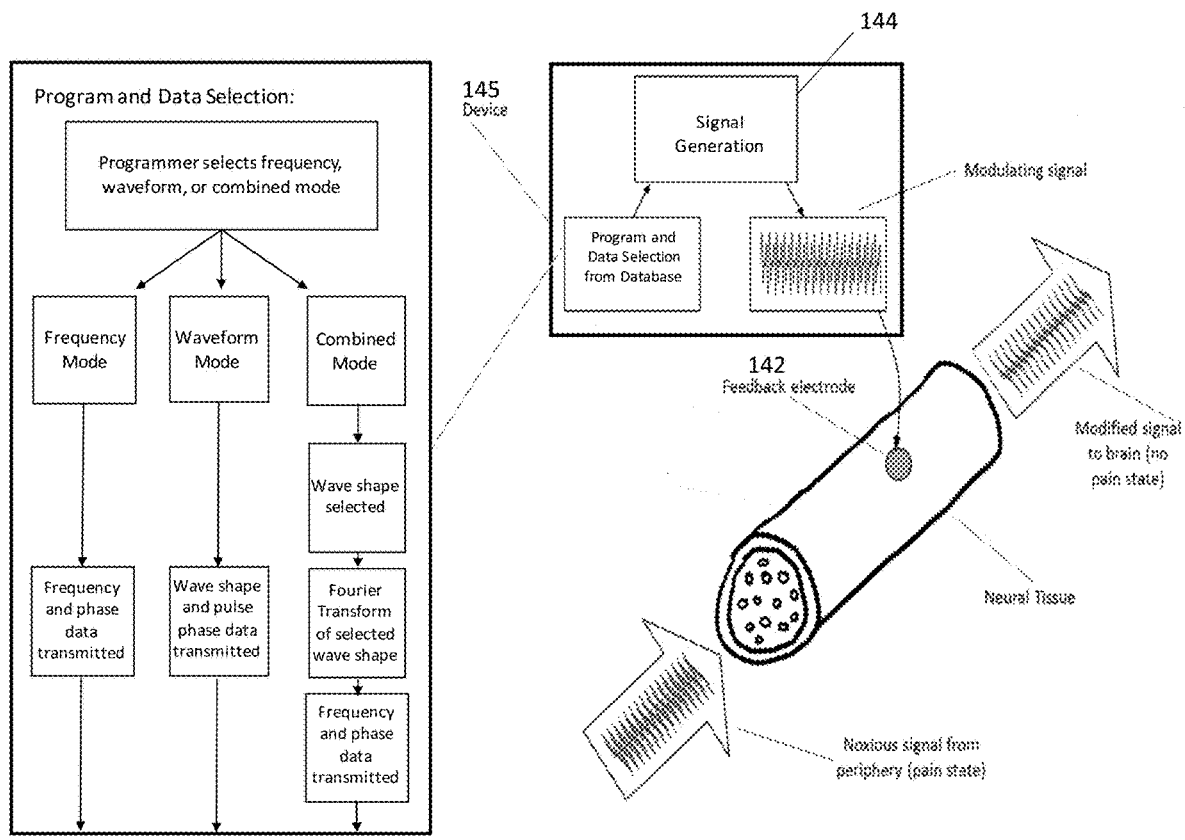
FIG. 14 is a conceptual illustration of a system that receives stimulation parameters from a neurostimulation database and modifies a noxious neural signal using a signal generated by one of the three modes outlined, in accordance with the disclosure.

FIG. 14 illustrates conceptually a system 145 that receives stimulation parameters from a neurostimulation database and, utilizing signal generator logic 144, generates a modulating signal generated by one of the three modes. In one embodiment, the system 145 is be capable of utilizing all three methods of stimulation, and allows for a programmer or user to select which method of stimulation is preferred, or, allows the user to decide between a frequency-based program from the neurostimulation database, a waveform hyperpolarization program, or a combined (waveform-frequency based) program to generate a modulating signal capable of modifying a noxious neural signal. With both frequency-based and waveform hyperpolarization programs of therapeutic neurostimulation, a neurostimulator device may generate signals through a programmable periodic timing circuit, such as a CMOS programmable timer. Such integrated circuit component function by taking an input value, herein defined as the "count parameter", a variable that informs the programmable counter of the number of events required to perform some action. In this embodiment, that action is passing an electrical signal to the stimulation leads. In one embodiment, a quartz piezoelectric oscillator made with a "fork-cut", and a fundamental frequency of 32.768 kHz for example, and labeled herein as $f_0$, will have a voltage passed through it from a power source. The resulting voltage oscillation of the crystal will be detected and counted by the CMOS programmable timer. The timer will receive an input variable from the database corresponding to the stimulation frequency, $f_s$. This variable will be the result of $f_0$ divided by $f_s$ and will be the count parameter. An example of such embodiment is illustrated by elements 114, 115, and 116 in FIG. 11. In one embodiment, to ensure accuracy of the signal for a count parameter that is not a whole number, the result of that division will be calculated to four decimal places. The nearest whole number larger than the count parameter will be counted a number of time equivalent to the four numbers after the decimal place of the count parameter multiplied by 10,000. The nearest whole number smaller than the count parameter will be counted a number of times equivalent to 10,000 minus the previous number. This will ensure a frequency within a range of 0.00001 Hz of the desired frequency. An example is shown below:

$$\frac{f_0}{f_s} = \text{Count Parameter}$$

$$\text{Ex. } f_0 = 32.768 \text{ kHz } f_s = 319$$

$$\text{Count Parameter} = \frac{32768}{319} = 102.7210$$

The decimal "0.7210" should be multiplied by 10,000, giving a result of 7210. This is the number of times the counter is to count to reach 103. The timer should then count to 102, for a total of 2790 (10000−7210) times. This results in an average frequency of 102.7210 Hz, as (103*7210)+(102*2790)/10000 is equal to 102.7210.

In addition to accepting the aforementioned "count parameter" that sets the frequency of the stimulation, the device will have a "phase parameter" that allows the signal to be shifted through its phase temporally. In one embodiment this will be performed by a separate programmable timing circuit, however it may not be a periodic integrated circuit. The timing circuit will take whatever value it is programmed to, where the input can be a percentage of the period ($1/f_s$), a fraction of $2\pi$, or a hard numeric value between 0 and the period. The resolution of the phase shift is based on the fundamental frequency of the oscillator $f_0$, with the smallest allowed time step equal to the period ($1/f_s$) divided by $f_0$. This value will be sent to a programmable timing circuit that will delay the release of the signal by the assigned phase shift. This value, when replaced with a new number, will reset the counter, shifting the signal by creating a new delay phase. Once the assigned number is reached by the counter that allows for proper timed delivery, the counter's value will not be changed and it will remain in an open state allowing the signal to be freely transmitted. This phase parameter can either be programmed and shifted by a programmer, or can be altered by the end-user to allow for adjustment throughout use of the device to optimize pain relief.

Figure 23A:
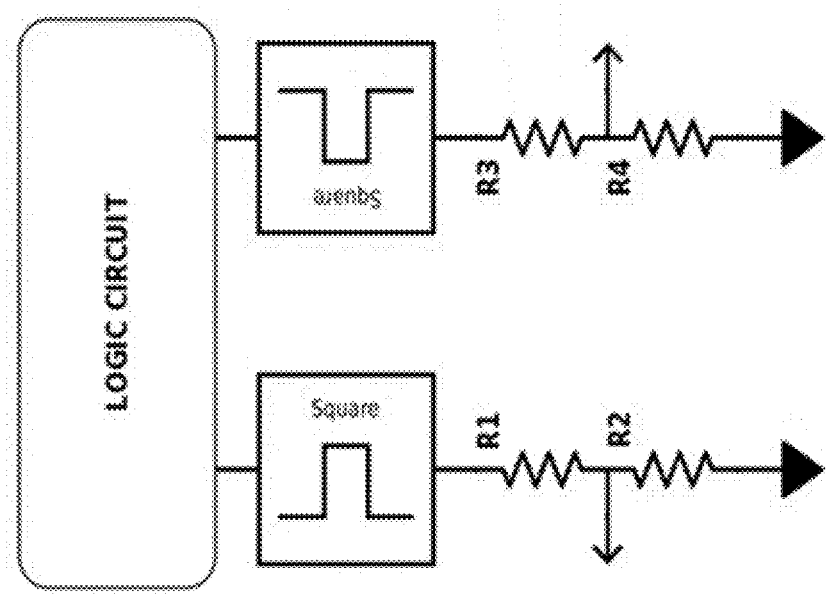
FIG. 23A-B are device circuit schematics of the signal generating circuits that may be utilized with a system, in accordance with the disclosure.
Figure 23B:
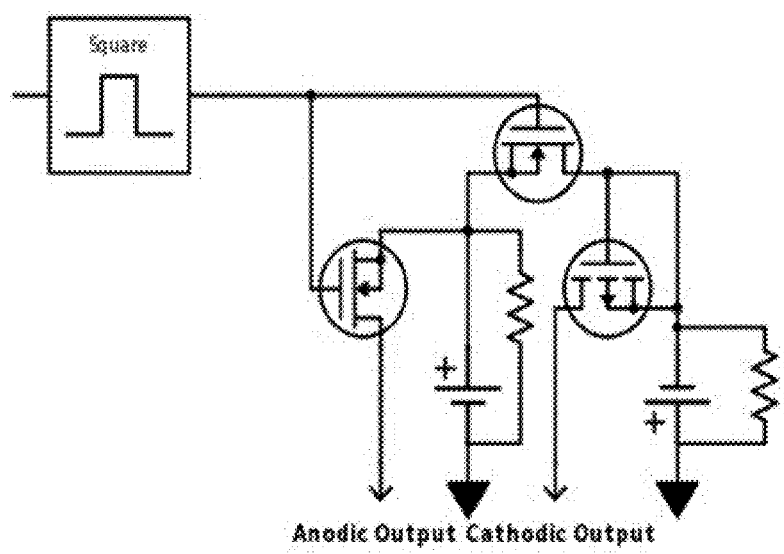

In another embodiment, the frequency and phase shift parameters may be calculated by a digital microcircuit in the programming device. This device 117 will then transmit a signal with information regarding frequency, amplitude, and phase shift to the implanted device. The amplitude information will be coded as a resistance value for a programmable resistor that will step up or down the voltage from a power supply in the device. The frequency and phase information will be passed to a pair of logical level transistors (N or P channel MOSFETs). These circuitry components may be programmed to either open or close with a digital or binary signal to help minimize the size of the implantable device while enabling it to send complex, true sinusoid derived waves. Exemplary embodiment are illustrated in FIG. 23A-B.

In another embodiment, the implantable device as described in both of the above embodiments of signal generation, may have a sine wave inverter in the device, allowing for generation of real sinusoids to the electrode leads thereby enabling better destructive interference with the frequency or frequencies of interest.

In these embodiments, the electrode array 119 used to deliver the signal necessary to prevent the action potential from firing may be set to limit extraneous field lines. This may be done by arranging electrodes of opposite polarity on each side of the electrode that provides the main modulating interfering field. This multipolar field arrangement will shape and steer the interfering field lines around a particular spatial region of the neural tissue that is being stimulated. This prevents excessive field strength in undesired extracellular fluid and keeps the field closer to the shape of the neural anatomy. This technique also mitigates the creation of an artificial charge sink somewhere else in the neuron.

It is known that any external signal used to modulate neuronal responses propagates bi-directionally. This may pose an issue because the modulating signal delivered by the device may have the frequency components characteristic of the pain signal. As such, when the modulating signal descends down the neural tissue, it will destructively interfere with the incoming pain signal as expected. It may, however, also travel up to the brain and may be perceived as pain because the signal carries the characteristic frequency that is processed as nociception. In order to address this, the modulating signal may consist of a waveform that has the opposite amplitude while oscillating at the proper frequency and phase characteristic of the pain signal. This implies sending a stepwise negative function with the proper frequency to the spinal cord to interfere with the selected frequency of that signal. This process may result in the neuronal membrane hyperpolarizing for a brief moment and therefore will stop the depolarization that has occurred from neuronal oscillations at a specific frequency.

In another embodiment, the modulating unidirectional hyperpolarizing signal is obtained by creating a virtual anode. This is created by using a cathode in conjunction with neighboring asymmetric anodes as described by Basser and Roth in a publication entitled *New Currents in Electrical Stimulation of Excitable Tissues* in the Annual Review of Biomedical Engineering, 2000; 02:377-397. The neighboring anodes create an area receptive for positive charge, which causes a build-up of anodic charge on the neuronal membrane despite no positive current is being delivered directly to the membrane; thus generating a virtual anode. One embodiment of this virtual anode for hyperpolarization of the neuron involves an electrode array in which a cathode is flanked by anodes on both sides. The electrode configuration is aligned along the length of the neuron's axon. The distance between the one of the flanking anodes (proximal) and the cathode is smaller than the distance between the other flanking anode (distal) and the cathode. The asymmetry creates a hyperpolarization of the membrane that prevents the propagation of an action potential at the proximal side. It will be obvious to the skilled in the art that this virtual anode can be created through various electrode configurations. These include an orthogonally placed cathode and anode, various insulated cuff electrode, and other cathode-anode pairs.

Figure 15:
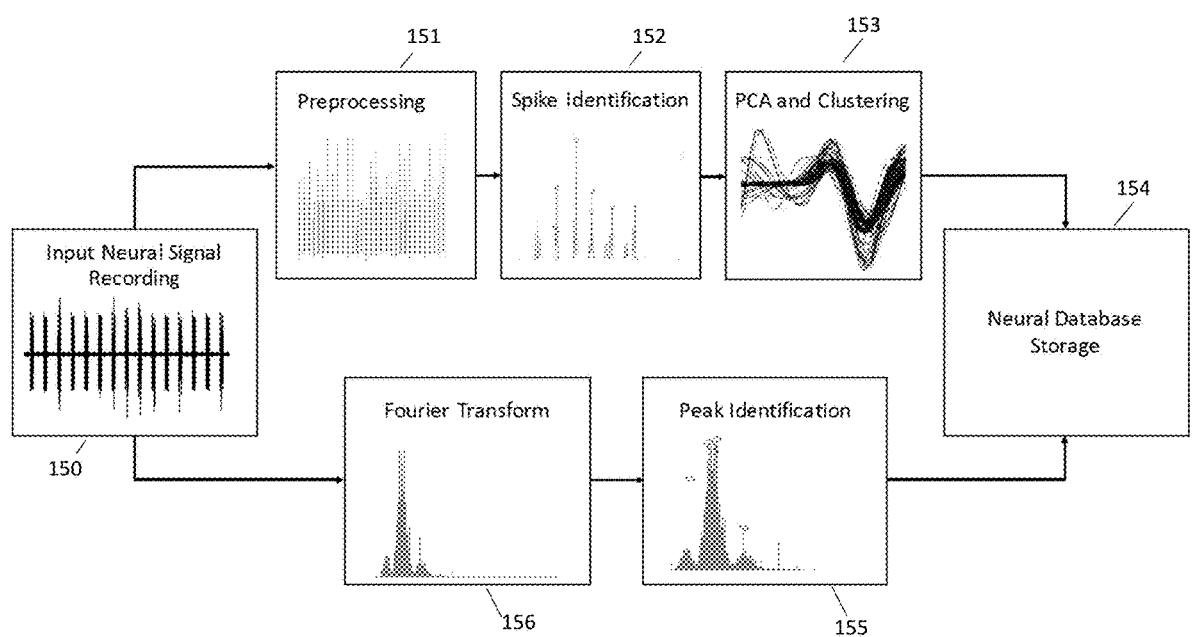
FIG. 15 is a conceptual illustration of the two individual or parallel data analysis processes used by the system, in accordance with the disclosure.

FIG. 15 illustrates conceptually the two individual or parallel data analysis processes used by the system to generate a biological data driven stimulation protocol for storage in the neural database and access by the programmable signal-compensating stimulation device for therapeutic neuromodulation. Such processes may be performed by execution of appropriate algorithms, as described herein, by analysis and signal correction module 100 of neurostimulator of system 45. The initial step of the characterizing nociceptive signals for therapeutic purposes is acquiring a neural signal, as indicated in block 150 of FIG. 15. In one embodiment, the signal can be acquired using a recording electrode in the extracellular space around a neuron. The advantage of this recording technique is its non-invasive nature with respect to the axon. A contact on a multi-contact stimulating electrode of either cylindrical or paddle shape can be assigned to record the extracellular potential.

In another embodiment, the signal can be recorded intracellularly by physically impaling the axon of a neuron using the minimally invasive technique of microneurography. This method involves the placement of transcutaneous recording microtungsten electrodes into a nerve, and may be performed on peripheral nerves outside of the spine. It will be obvious to those skilled in the art that other neurographic recording methods exist that can be utilized by the biological neurostimulation device for acquiring a signal for processing.

Signal acquisition may occur before implantation to establish a database, but may also be integrated as part of the data driven neurostimulation system in order to develop an ever-growing database. To understand the difference between no-pain and nociceptive signals, two recordings may be obtained. The first of the recordings may come from a subject with the nociceptive signal present. The second baseline recording may come from healthy neurons in the body, which can be obtained when a patient is in any of a no-pain state, during sleeping, under an anesthetic agent, by analgesic medication, or from a healthy subject separate from the affected individual. It will be clear to those skilled in the art that this signal collection could be performed in any of the spinal cord, a dorsal root ganglion, a peripheral nerve, or any combination of these.

Following acquisition, a recorded signal may be preprocessed, as indicated in block 151 of FIG. 15. In embodiments, the preprocessed signal may be amplified and filtered before undergoing spike identification. The amplification process may be performed using any number of various amplifier circuitry designs. In the simplest embodiment, amplification is done with a gain amplifier set to multiply the signal based on various circuit component values, the foregoing description not intended to limit the scope of amplification circuitry applicable in the pre-processing of the neural signal.

In one embodiment, following amplification, the signal will undergo filtering to eliminate noise and other unwanted elements. Methods for filtering vary widely. In a particular embodiment, the Teager energy operator may be employed to increase the signal to noise ratio of the signal prior to analysis. The equation for the Teager energy operator in its non-differential form is:

$$\psi\{x[n]\}=x^2[n]-x[n-k]x[n+k]$$

It is clear to those skilled in the art, that the Teager energy operator itself can take many forms and that it is one of a vast number of noise filtering methods. Its use here is not intended to limit the scope of the method of filtering. Following the filtering, a smoothing window may be applied to force the beginning and end of the signal to be zero. Any smoothing window may be used, however Hamming windows, Hann windows, and flattop windows are ideal for amplitude measurements and noise reduction. The Hamming window is most apt for this pre-processing, as it functions to equalize the initial and final points in the signal to zero, allowing the waveform to more accurate represent a full complex sinusoid, resulting in less high frequency leakage, and creating a more accurate and clear power spectral density. Any of various smoothing windows may be used as appropriate to different signal types; the example of the Hamming window does not limit the scope of the method discussed.

The signal, once amplified and smoothed, will undergo a spike identification, as indicated in block 152 of FIG. 15. The method of spike detection may be dictated by design preferences, however the general theory underlies the method. In one embodiment, a threshold is set above the maximal level of noise, to avoid selecting any noise signal. Noise signal herein is defined as something not representative of a fully depolarized action potential, which is often caused by membrane oscillation, electrode movement, environmental electromagnetic fields, among other things, specific to the biological environment being recorded. The designation of the threshold can be set either arbitrarily by the user/programmer or can be set to alter as a fraction of maximal action potential amplitude. In both real-time and offline processing embodiments, either method of threshold determination is acceptable. In one method, once the threshold is set, the signal is differentiated to look for locations where its derivative equals zero, marking a point of slope change. In another method, the voltage at a point x, is evaluated relative to two other points x-1 and x-2. If x<x-1 and x-2<x-1, then x-1 is a peak. Upon detection of the peak, the width of the spike must be determined and stored. In one embodiment, the user determines the spike width arbitrarily. While this might work when there is prior data to support a spike width, an adaptive method may be optimal. An adaptive method of spike width determination locates the nearest negative peaks to the identified spike through its second derivative and the corresponding zero value points. Once a spike is identified, its voltage information is stored as a matrix variable. The aforementioned methods for spike identification are discussed to serve as examples of methods intended to be used, and are not meant to limit the scope of the methods described for pre-processing.

A signal, after recording or preprocessing, may undergo robust signal analysis to determine components of the signal biologically relevant to the patient's pain state. The temporal signal, after preprocessing may undergo a transformation into the frequency domain, as indicated in block 156 of FIG. 15. This process can be accomplished by a number of transforms, the most notable being the Fourier Transform, and the Hilbert Transform. In embodiments, the signal may undergo a discrete Fourier Transform (DFT). The Fourier Transform is a mathematical function used to convert a temporal signal into its sinusoidal components. The pair of equations governing the Fourier transform is as follows:

$$f(x) = \int_{-\infty}^{\infty} F(k)e^{2\pi i k x} dk$$

$$F(k) = \int_{-\infty}^{\infty} f(x)e^{-2\pi i k x} dx$$

wherein the top equation represents the conversion of a discrete time signal F(k) and its conversion to a complex signal in the frequency domain f(x) while the bottom equation represents the conversion from the frequency domain back to the time domain. As the signal is converted to the frequency domain, it is broken down into a summation of sinusoids with distinct frequencies (f), amplitudes (A), and phases ($\phi$).

The result of the Fourier transform applied to a real time signal is a series of complex numbers in the form of A+Bj. The square of the absolute value of this complex number is plotted for each frequency normalized against that frequency as a function of frequency, such plot known as the power spectral density. The analysis and signal correction module 100 performs the method for frequency analysis and power spectral density plotting as well as the Fourier shift to evaluate the positive frequency components, with the frequency range set from zero to the sampling frequency ($F_s$) divided by the number of elements in the series ($F_s/N$). The method for selecting which frequencies are characteristic or fundamental to the signal can be performed in several different ways.

The selection of characteristic frequencies of the pain state may be performed based on a comparison between the Fourier transform of pain and no-pain states, as indicated in block 155 of FIG. 15. The power spectral densities derived from both pain and no-pain signals may be compared at each frequency to find specific frequencies that show the most difference in signal contribution between pain and no-pain signals. The differences between power signals may be evaluated statistically to determine the average difference in the spectra and its variance, allowing for determination of frequencies that are statistically significantly altered between the pain and no pain states. Other methods for determining the difference between the power spectral densities may be used. The described technique is not meant to limit the scope of the methods described herein.

In another embodiment, the method for signal analysis may include wave shape analysis and principle component analysis (PCA), as indicated in block 153 of FIG. 15, either as the main analytical process or in conjunction with frequency domain transformation. The PCA process may begin with alignment of the waveforms as detected and stored during the spike identification step. Spike alignment may occur by multiple methods. One method is to align the spikes on their initial peak. This represents the most efficient method as the data corresponding to the exact locations of the peak have been calculated and stored in the spike identification step. Alternative methods include alignment along any characteristic point of the wave shape including the start, end, and/or any zero crossing points.

The next analytical step is completion of a principal component analysis. The principal component serves to measure covariance between the spikes and to create representative vectors. Following the principal component analysis, a clustering algorithm may be performed to isolate the various common waveforms between the scores from the principal component analysis.

Algorithms for clustering analysis are extremely diverse. The clustering analysis can have the number of clusters to create a set by the user or can be created based on the number of principal components. The function governing this can follow preset algorithms such as Euclidean, Squared Euclidean, Standard Euclidean, City Block, Minkowski, Chebychev, Mahalanobis, Cosine, Spearman, Hamming, Jaccard, or any custom function designed and set by the user. A linkage algorithm determines connectivity between data points to establish the clusters and may be implemented with different embodiments, including but not limited to: Average, Centroid, Complete, Median, Single, Ward, and Weighted. The clustering algorithm can be customized as needed especially in an offline analysis embodiment.

Figure 16:
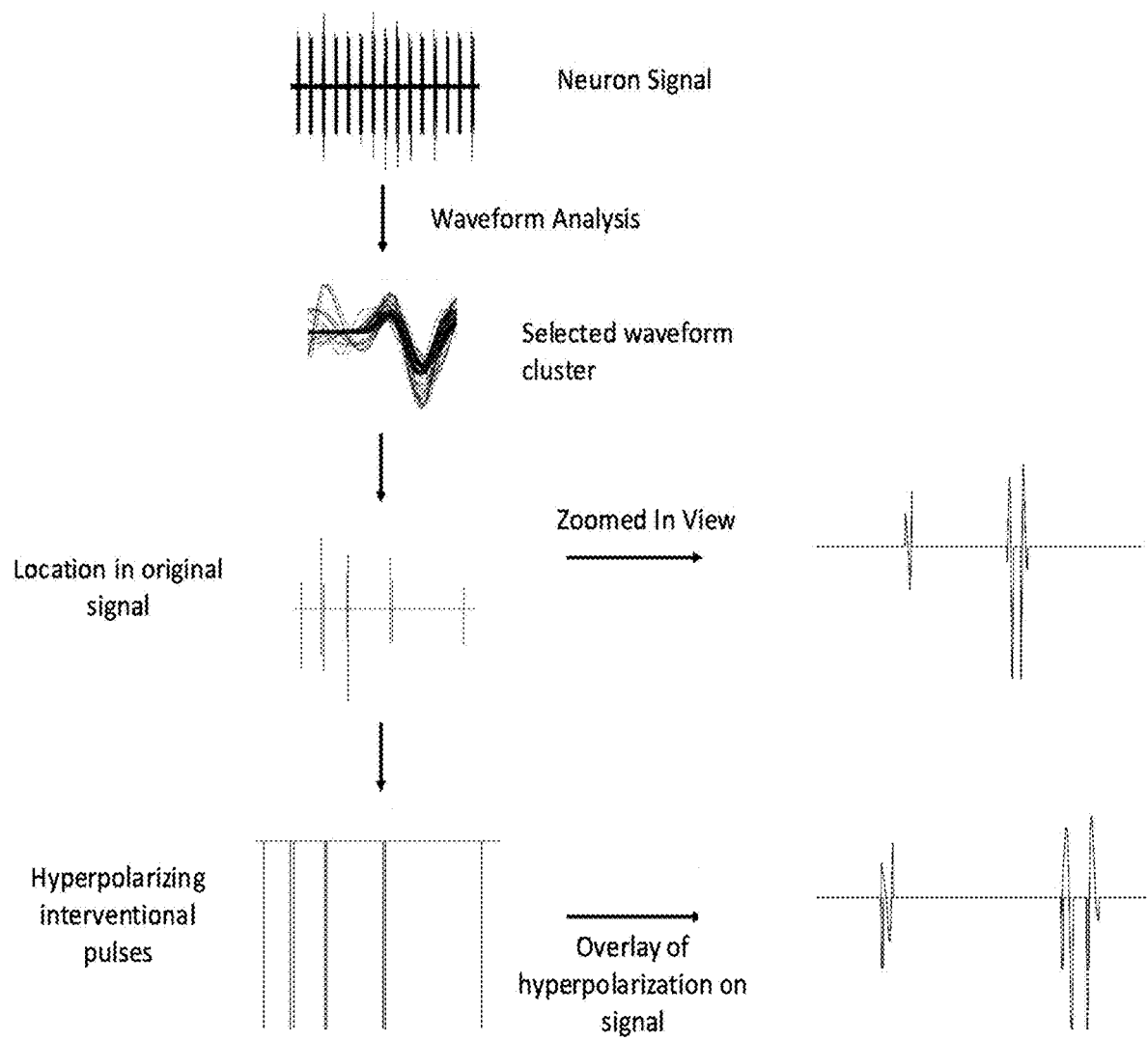
FIG. 16 is a flow chart illustrating conceptually the process waveform analysis including PCA and clustering. This illustration also displays how a hyperpolarizing signal can be generated from this information, in accordance with the disclosure.

FIG. 16 illustrates conceptually the process of waveform analysis including PCA and clustering and how a hyperpolarizing signal can be generated from this information.

Once these analyses have been performed, the clusters can be compared between pain and no pain states. The neurostimulation database device will evaluate the most populous clusters for both states and identify waveforms that have become more or less populous, new clusters that have been introduced to the signal, or clusters that have been deleted from the waveform.

Following the identification of important clusters, the waveforms of that cluster may further undergo a Fourier transform as described above. The characteristic frequencies will be determined as above for all waveforms in that cluster. The resulting list of characteristic frequencies will be averaged to determine what frequencies to deliver in therapy.

Upon completion of the above robust analysis, a therapeutic signal is created for delivery to the patient. The signal may be delivered in one of two methods. The first will be herein described as the interventional signal and will utilize a signal or signals which oscillate at a particular frequency or frequencies based on the Fourier transform analysis. The second will be referred to as the hyperpolarization signal and utilizes the information from waveform analysis to send a hyperpolarizing pulse to prevent action potential firing.

The interventional therapeutic signal utilizes the frequency and phase information gathered by the Fourier transform of either the entire signal or a cluster identified and analyzed in the waveform analysis. For a selected frequency in the Fourier transform, an inverse Fourier transform of the corresponding complex number over an array with length corresponding to the sampling frequency times the period will give one full cycle of the proper sinusoid for intervention. The information regarding this sinusoid is transmitted to the implanted generator device 42 where it is inverted and delivered to the neurons via leads 40.

One or more frequencies may be utilized to eliminate the noxious component in a signal of the neurons. In the current embodiment, the waveform delivered to the neuron is aligned such that it is approximately of the opposite amplitude of the same frequency wave in the biological signal. This alignment parameter is known as the phase of the wave and can take on any value from 0 to the period of the wave. Thus, one of the compensating waveforms will require a tuning method, wherein the phase of the waveform can be shifted throughout its period to ensure it aligns with the half-period shift of the biological signal. The remaining signals can be phase shifted relative to the first one based on their phase from the complex argument of the Fourier transform. This phase-shifting parameter represents a new programmable variable in a stimulation protocol that is distinct from other frequently used parameters such as frequency, amplitude, or pulse width, and is illustrated in FIG. 6.

Comparatively, current spinal cord stimulation protocols, while claiming to stimulate with frequencies containing units of Hertz (Hz), utilize a pulsatile stimulation protocol which is better considered as a rate. The "50 Hz" spinal cord stimulation that is well-established in the field comprises pulse trains with on and off phases, wherein the combined on and off time totals 1/50 seconds (0.02 seconds). In the stimulation method described herein, the pulse width of the on phase is set arbitrarily, often being set to 200 µs. The system described herein utilizes sinusoid-based signals that can be modeled as a single sinusoid wave or a sum of sinusoid waves. The "pulse width" generated by the disclosed biological neurostimulation device will be a function inversely proportional to the frequency of stimulation, rather than a parametric variable with an operational range of zero to half the period as in known devices. This results in the aspects of the signal able to be programmed being the amplitude and the newly introduced phase shift variable.

For the disclosed frequency-based Fourier transform method of signal generation, the device 42 may utilize sinusoidal signals in a frequency range of zero to 5,000 Hz. The other programmable parameter in the disclosed signal generation method may be the amplitude of the resulting compensating signal, which is expected to remain significantly lower than currently used in spinal and peripheral nerve stimulation protocols.

In another embodiment, the delivery of therapeutic signal is done in a discretized form, based on the waveform analysis alone. In this embodiment, the selected cluster or clusters of interest are identified in the initial time-based analysis and the space between them, herein referred to as the latency, determined. The period over which a discernable pattern is repeated is determined and referred to herein as the event period. The device 42 will deliver a series of hyperpolarizing pulses to eliminate the corresponding waveforms in the identified clusters. As in the above embodiment, a parameter capable of shifting the waveform throughout its phase is programmable and may be controlled with tuning logic or circuitry that is able to shift the signal compensating pulses between zero and the event period.

Figure 17A:
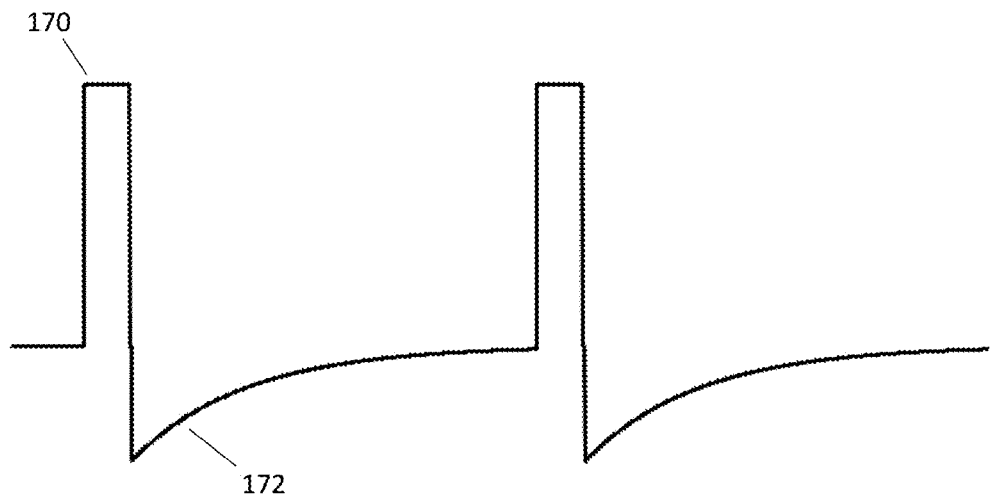
FIG. 17A-B illustrates conceptually a representative biphasic signals with an anodic front for modulation (first phase) and cathodic balance (second phase), in accordance with the disclosure.
Figure 17B:
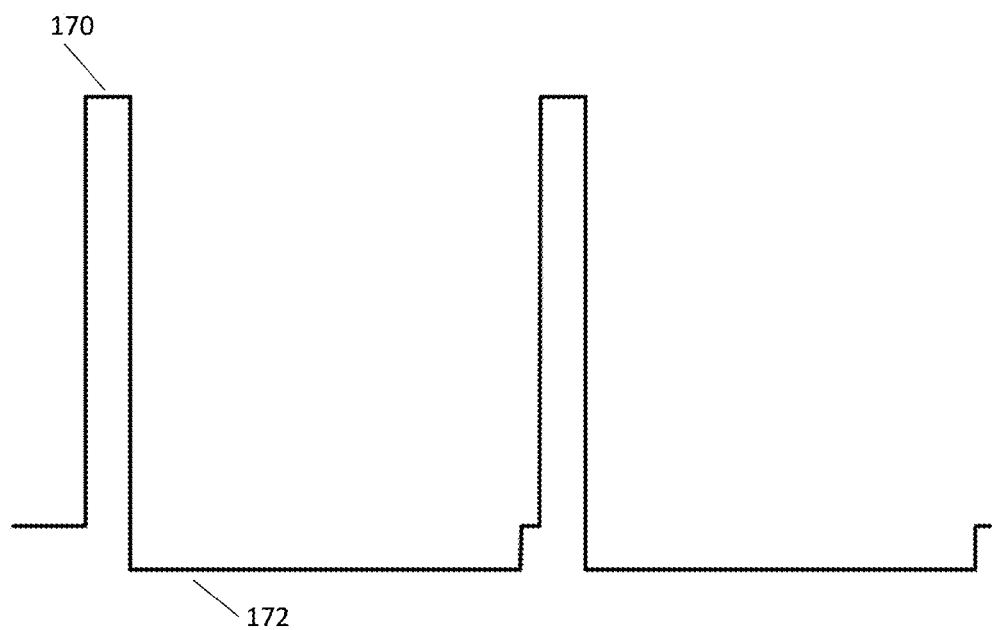

FIGS. 17A-B illustrate representative biphasic signals with an anodic front 170 for modulation (first phase) and cathodic balance 172 (second phase). In the disclosed stimulation method, the modulating signal consists of an extracellular anodic pulse (positive voltage and current) to create hyperpolarization of the neuron. The anodic pulse 170 is followed by a cathodic pulse 172 (negative voltage and current), as illustrated in FIG. 17A-B to balance the current flux experienced by the cells and to prevent undesired reduction or oxidation processes that may be disruptive to cell function. The cathodic pulse may have an amplitude necessary to allow for charge balancing while remaining under the threshold that generates an action potential. The charge-balancing cathodic pulse may be implemented in multiple different techniques. In one embodiment, the cathodic pulse is allowed to dissipate over an extended period of time, in what is called passive charge balancing. In another embodiment, called active charge balancing, the dissipation of the cathodic pulse is controlled over a certain time period by the device 42. It will be obvious to the skilled in the art that the waveforms used in creating the charge balancing cathodic pulse may be varying in shape. These include sinusoids, Gaussian pulses, triangular pulses, trapezoidal pulses, linear ramp (increasing or decreasing) pulses, exponential ramp (increasing or decreasing) pulses, or any pulse train that can be created as the time steps between voltage changes go to infinity and the function becomes a continuous integrated function.

EXAMPLE 1

Computer-Based Simulation of Concept

Figure 18A:
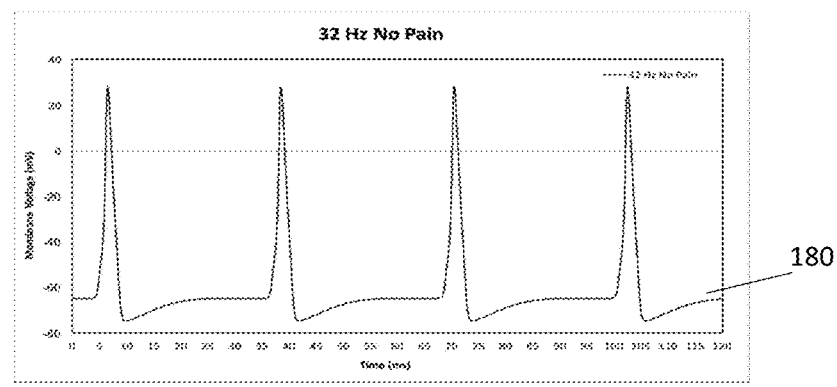
FIG. 18A-C illustrate conceptually results from a simulation of action potentials generated upon stimulation of a model neuron, in accordance with the disclosure.
Figure 18B:
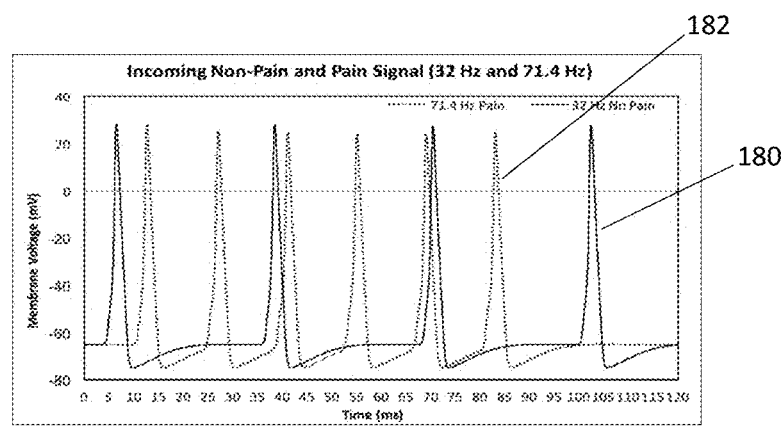
Figure 18C:
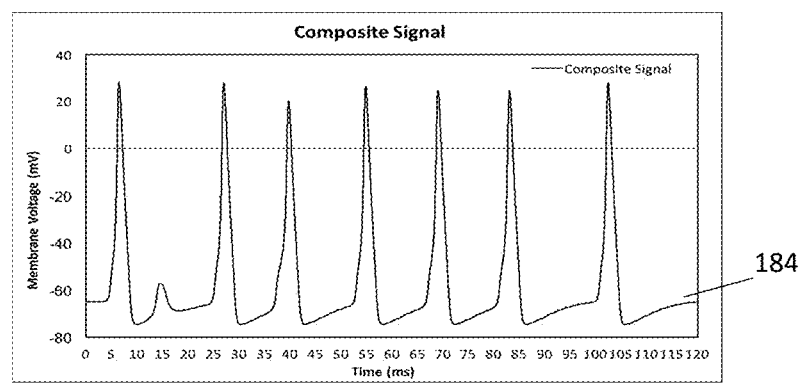

A computer simulation using the software Neuron version 7.4 was carried out to validate the principle of operation of the disclosed concepts. A model was modified from an open source model for extracellular stimulation (www.neuron.yale.edu/phpBB/viewtopic.php?f=15&t=1937). The model utilized a single neuron fiber, consisting of a dendrite, soma, and axon, with one axonal section being able to receive extracellular stimulation. The neuron properties used, including diameter, resistance, and capacitance, were in line with values published by Ackermann, Foldes, Bhadra, and Kilgore in "Effect of Bipolar Cuff Electrode Design on Block Threshold in High-Frequency Electrical Neural Conduction Block" in IEEE Transactions on Neural Systems and Rehabilitation Engineering, 2009; 17:469-77. The neuron was modeled with the standard Hodgkin-Huxley equation, using passive channel mechanics. Sensory stimuli that models a no-pain state and a pain state were simulated by inputting a train of pulses at the soma or at the dendrite or axon near the soma at a prescribed frequency. The resulting membrane depolarization was measured on the axon distal to the modifying extracellular stimulus. FIG. 18A-C illustrate conceptually the results from a simulation of action potentials generated upon stimulation of a model neuron. FIG. 18A illustrates action potentials corresponding to a no-pain state (32 Hz).

FIG. 18B illustrates action potentials for the no-pain state (32 Hz) and those generated by a noxious stimulus (71.4 Hz). FIG. 18C illustrates the action potential generated when the action potentials in FIG. 18B are combined in the neuron membrane. In FIGS. 18A-18C the simulated action potentials are produced from two stimuli as they are seen at the distal axon. The stimuli are located at the soma and the axon directly connected to the soma and are firing pulses at 32 Hz and 71.4 Hz respectively. The 32 Hz signal illustrated in FIG. 18A is meant to represent a no-pain signal 180 such as standard proprioception from environmental interaction. Another stimulus that is firing at a rate of 71.4 Hz, as illustrated in FIG. 18B, represents the signal 182 generated by a noxious stimulus. The result of both signals oscillating at different frequencies results in a unique waveform that is the composite action potential, as illustrated in FIG. 18C. This composite signal 184 is representative of the waveform seen by the brain during a pain state. The no-pain signal comprises four action potentials in the time window used in the simulation, while the noxious signal comprises six action potentials in the same time window. When the no-pain signal is combined with the signal from the noxious stimulus simultaneously, the resulting composite signal that represents the pain state comprises seven action potentials. In this example, one of the action potentials of the noxious signal at 71.4 Hz has been suppressed and two of each stimulus have been combined, as illustrated in FIG. 18C. This is expected because of the inherent behavior of neurons. A neuron does not fully depolarize to produce an action potential while it is in a refractory period, and if two stimuli happen to coincide, then only one action potential will result.

Figure 19A:
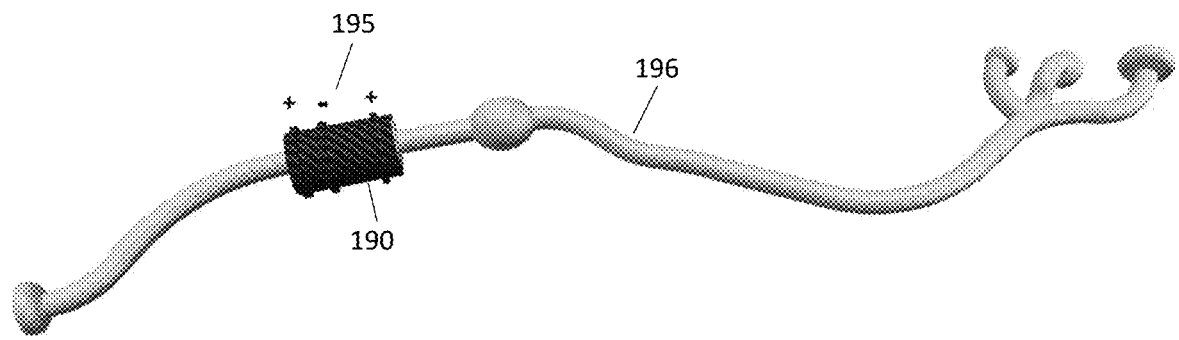
FIG. 19A-B illustrates conceptually a three-dimensional models of peripheral neuron with the tripolar electrode and cuff located on the axon to demonstrate location of extracellular stimulation and a close up view of the tripolar electrode showing anodic and cathodic connections, in accordance with the disclosure.
Figure 19B:
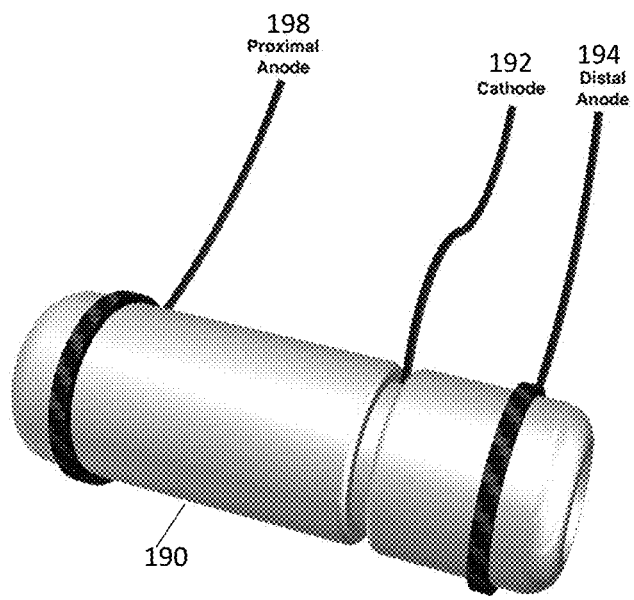

FIG. 19A-B illustrate conceptually a three-dimensional models of peripheral neuron with the tripolar electrode and cuff located on the axon to demonstrate location of extracellular stimulation and a close up view of the tripolar electrode showing anodic and cathodic connections. The device and its function were simulated by generating a modifying extracellular signal on the axon at an arbitrary length distal to the sensory stimulus. The extracellular stimulating electrode used for modulating the pain state signal to remove the effects of the noxious stimuli comprises a tripolar electrodes 195 in conjunction with an insulated cuff 190, as illustrated in FIG. 19A-B. The tripolar electrode consisted of a cathode flanked by two anodes. The spacing between the cathode and the distal anode is smaller than the distance between the cathode and the anode proximal to the soma. The orientation of the tripole electrodes 195 is shown in FIG. 19A. It was set in the afferent pathway and was oriented parallel to the length of the axon 196. The axon feels the effects of cathodic stimulation directly below the cathode and the transfer of charge through the extracellular fluid to the anodes creates a strong virtual anode in the distal axon, interfering with the noxious signal. In this example, a rectangular pulse was sent through the tripole with a pulse width in the 100 µs to 1000 µs range and current values in the 100 nA to 1 mA range. It will be obvious to the skilled in the art that other waveforms may be used as modulating signals, including sinusoids, Gaussian pulses, triangular pulses, trapezoidal pulses, linear ramp (increasing or decreasing) pulses, exponential ramp (increasing or decreasing) pulses, or any pulse train that can be created as the time steps between voltage changes go to infinity and the function becomes a continuous integrated function.

Figure 20A:
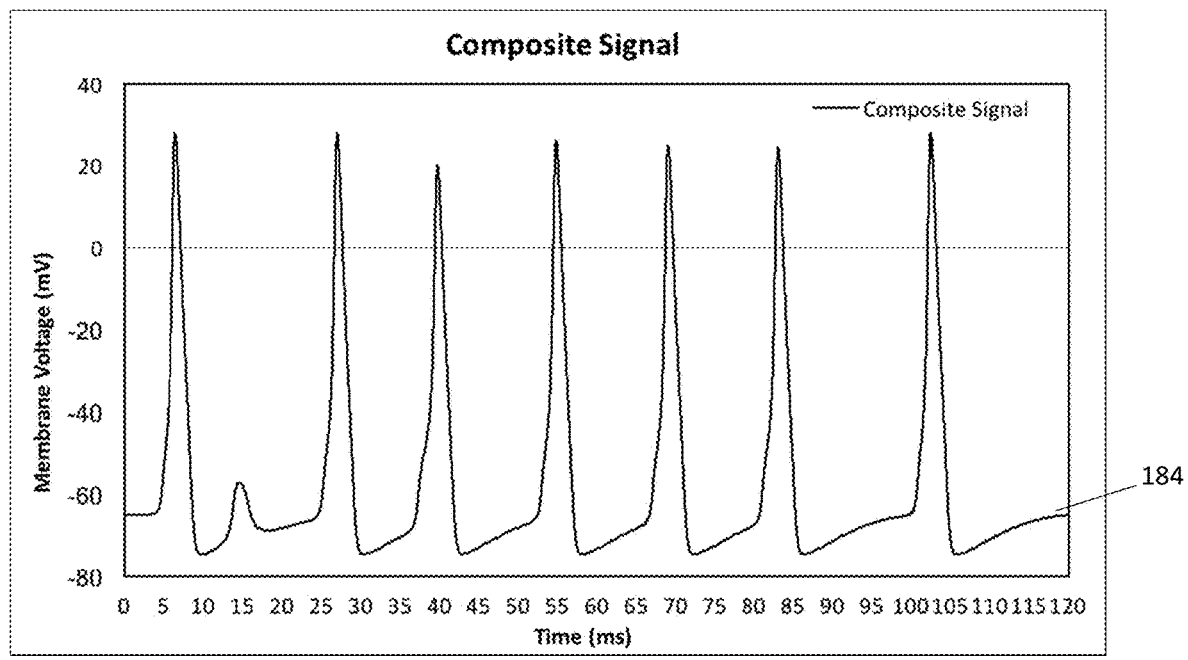
FIG. 20A-B illustrates conceptually the results of simulations showing the effect of introducing an anodic modulating signal oscillating at 71.4 Hz, in accordance with the disclosure.
Figure 20B:
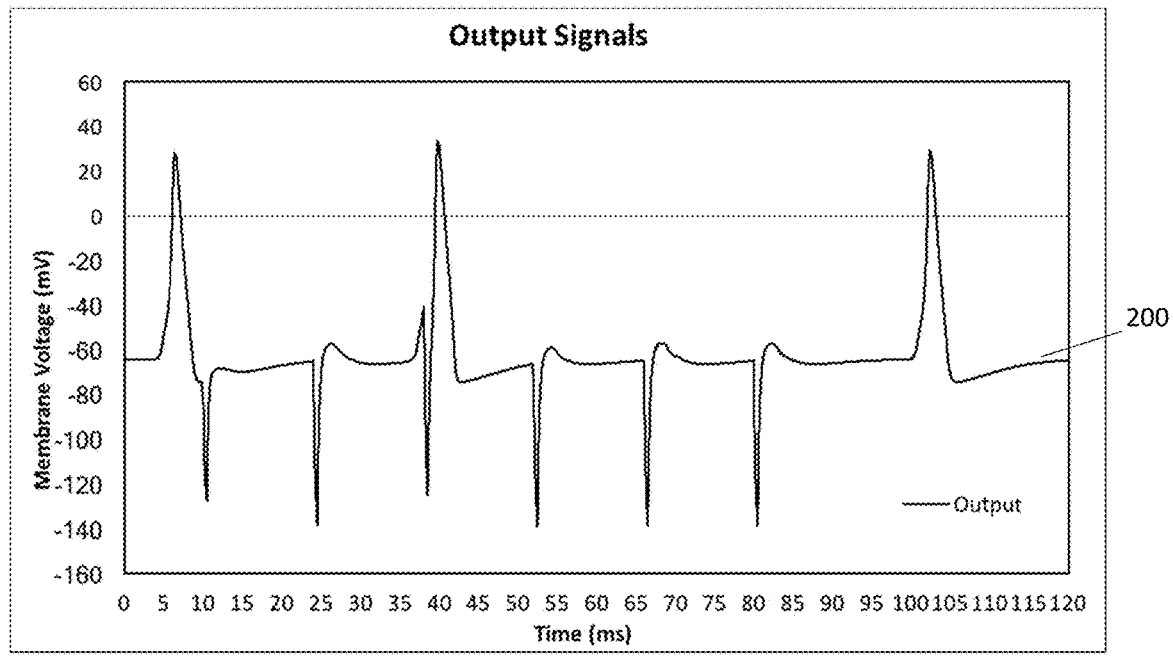

FIGS. 20A-B illustrate conceptually the results of simulations showing the effect of introducing an anodic modulating signal oscillating at 71.4 Hz. FIG. 20A is the composite neuronal action potentials that constitute the pain signal before the modulation and FIG. 20B is resulting signal after the anodic hyperpolarizing modulation at 71.4 Hz. The effect of the modulating signal on the pain signal is illustrated in FIG. 20A-B. These show that the extracellular electrode 195 is able to suppress the 71.4 Hz pulses. In this case, three out of the four action potentials produced individually by the 32 Hz stimulus are present, thus rendering a modified signal 200 that resembles the no-pain state, and more importantly, a signal in which the action potentials due to the noxious stimulus have been removed.

In summary, the simulations demonstrate that it is possible to selectively modulate a composite neuronal signal by creating an interfering electrical pulse that is tuned to a given frequency that corresponds to the oscillatory pattern of a noxious signal, rendering a result modified signal that reproduces the no-pain state with high fidelity.

EXAMPLE 2

In Vivo Proof of Concept Including Recording and Frequency-Domain Processing

An in vivo electrophysiology model experiment was performed in an anesthetized earthworm to examine the effects of hyperpolarizing anodic stimulation in a live biological system. The earthworm was anesthetized by immersion in a 10% ethanol bath for 7 to 10 minutes. A function generator (Accupulser A310, World Precision Instruments) was used to stimulate the ventral nerve cord of the earthworm via an extracellular electrode inserted orthogonally in the rostral end nearby the nerve cord. A microneurography kit (Neuron SpikerBox, Backyard Brains) was used to record the action potentials. The recording electrodes were inserted transcutaneously into the ventral nerve cord at the caudal end. A second electrode set to anodic modulation was also placed in the rostral end, nearby a cathodic electrode to mitigate synchronization issues. The function generator was set to generate a train of pulses at 1.6 Hz to stimulate the neuron via the cathode. The function generator was turned on with only the cathode connected. After 12 seconds, the anode was connected and the worm received the hyperpolarizing anodic modulation signal. After an additional 15 seconds the anode was disconnected and recording continued for 5 seconds. The recordings were plotted on a voltage vs. time graph in FIG. 21, which proves the efficacy of anodic stimulation for neuronal hyperpolarization as an effective method for selective frequency blockade in neuron action potential propagation.

Figure 21:
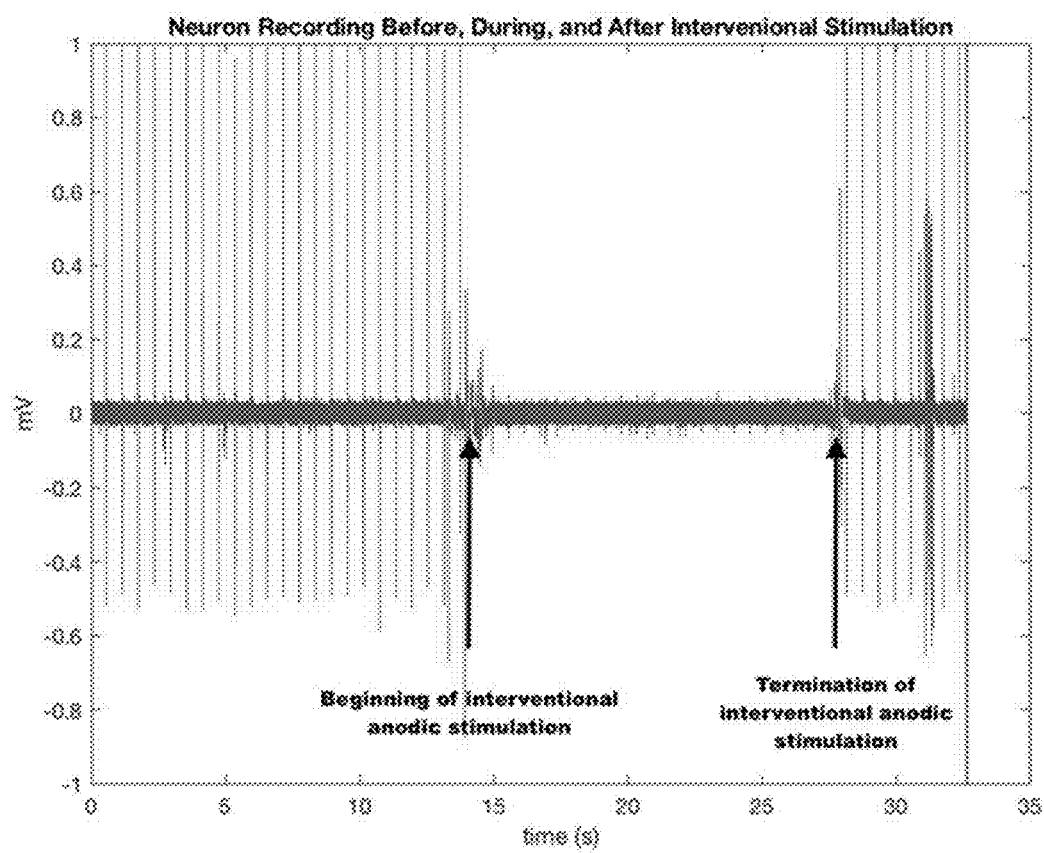
FIG. 21 illustrates conceptually recordings from the ventral nerve cord of an earthworm showing the efficacy of anodic stimulation for neuronal hyperpolarization as an effective method for selective frequency blockade in neuron action potential propagation, in accordance with the disclosure.
Figure 22A:
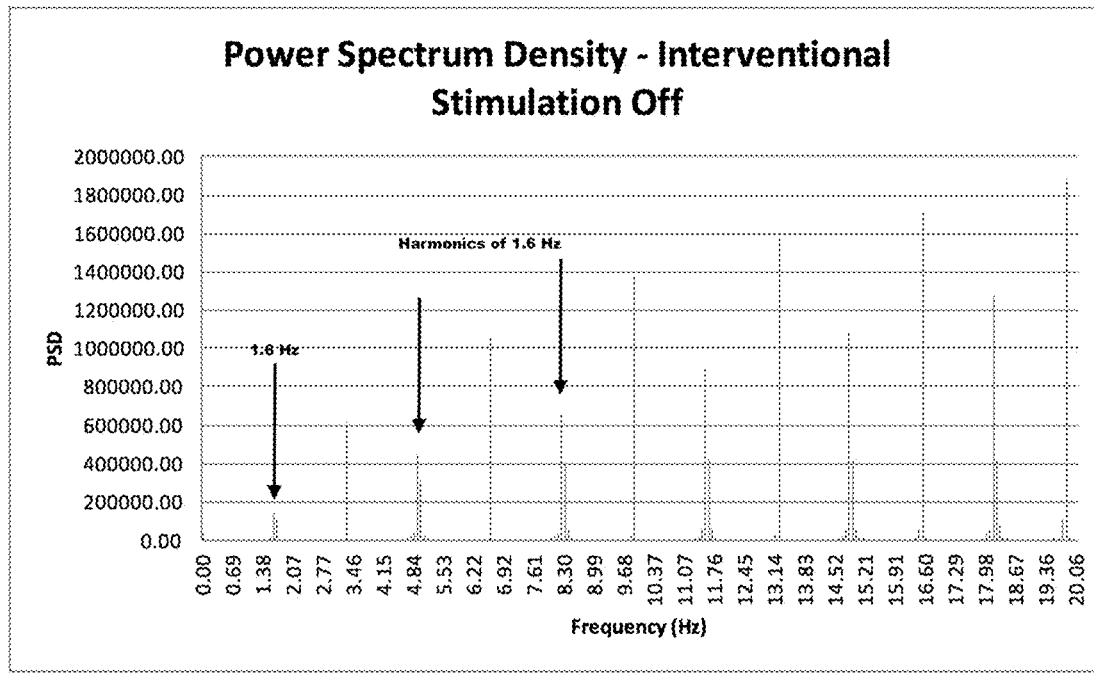
FIG. 22A illustrates conceptually a power spectral density frequency analysis via Fourier transform of the recording showing the analysis without anodic modulation (initial 10 seconds of recording in FIG. 21), in accordance with the disclosure.
Figure 22B:
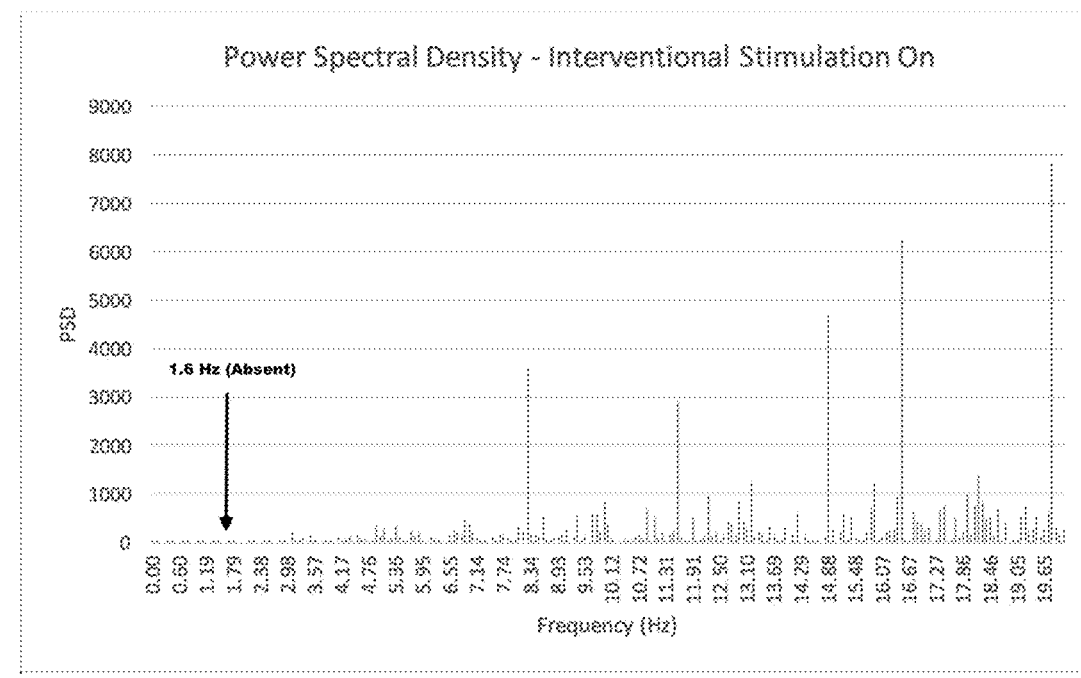
FIG. 22B illustrates conceptually a power spectral density frequency analysis via Fourier transform of the recording showing the analysis during anodic modulation (15 to 25 seconds time window in FIG. 21), in accordance with the disclosure.

This example proves that a hyperpolarizing signal provided by an anodic electrode inserted in the nerve, and tuned to the firing frequency of action potentials induced by an external stimulus, is able to interfere with the action potentials and stop their propagation. The amplitude of the anodic square wave was at least 50 mV, which is the voltage necessary for preventing neuron depolarization. As illustrated in FIG. 21, the introduction of the hyperpolarizing anode caused action potentials resulting from external cathodic stimulation to cease firing for the entire duration of the anodic modulation. Upon removing the anodic modulation, the action potentials return. The neuron recordings were also subjected to a power spectrum analysis as is intended by the device. FIG. 22A-B illustrates power spectral density frequency analysis via Fourier transform of the recordings. FIG. 22A shows the analysis without anodic modulation (initial 10 seconds of recording in FIG. 21). FIG. 22B shows the analysis during anodic modulation (15 to 25 seconds time window in FIG. 21). The absence of a spike at 1.6 Hz in this spectrum indicates removal of the desired signal. The results of the power spectrum analysis from time 0 to 10 seconds and 15 seconds to 25 seconds are illustrated in FIG. 22A-B, with the most prominent peaks and peaks of interest highlighted and labeled. The figures show the contributions of different frequencies to the overall signal and are clearly distinct from each other. Most notably, the peak seen at 1.6 Hz in the analysis of the initial 10 seconds, as illustrated in FIG. 22A, is not present in the graph of the 15 to 25 seconds window, where anodic modulation was present, as illustrated in FIG. 22B.

In summary, the in vivo experiments demonstrate that it is possible to selectively modulate a neuronal signal by creating an interfering electrical pulse that is tuned to a given frequency that corresponds to the oscillatory pattern of a noxious signal, rendering a signal that reproduces the non-stimulated state with high fidelity.

EXAMPLE 3

Description of Prototype Device

Figure 24:
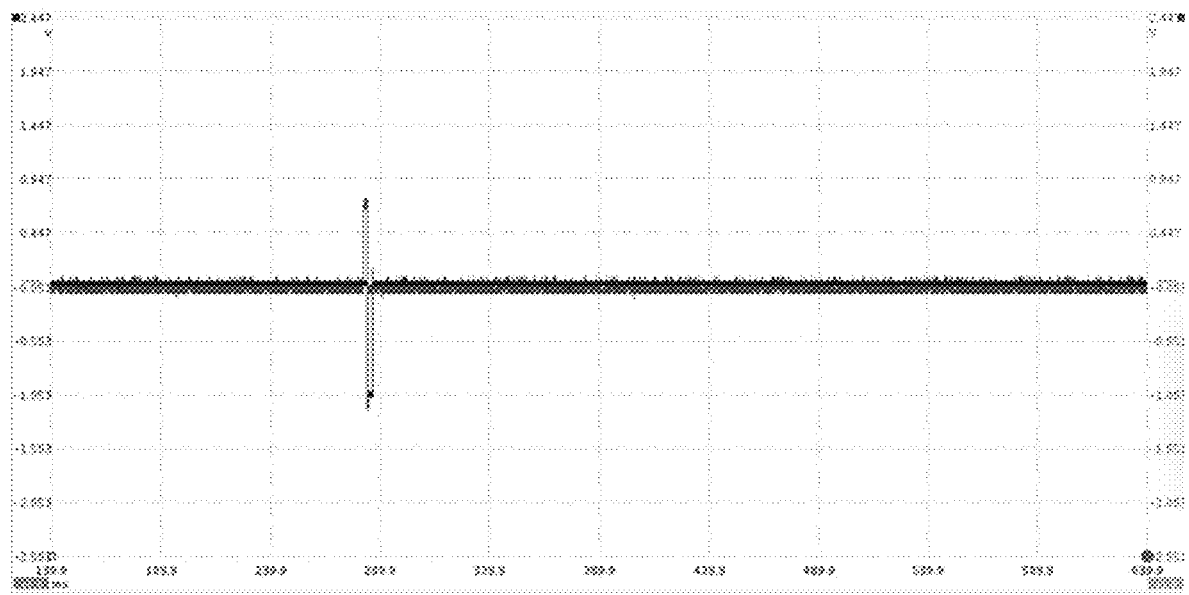
FIG. 24 illustrates conceptually an actively charge balanced, biphasic, anodic lead waveform created by the device as recorded in an oscilloscope, in accordance with the disclosure.

An alpha-prototype of the device has been developed to demonstrate its practicality and potential. The prototype was created utilizing a low-cost, programmable integrated circuit (Adafruit Industries) and various circuit components. FIG. 23A-B are device circuit schematics of the signal generating circuits that may be utilized with a system. FIG. 24 illustrates conceptually an actively charge balanced, biphasic, anodic lead waveform created by the device as recorded in an oscilloscope.

As illustrated in FIG. 23A, the prototype comprises three main components: a power source, a logic circuit, and signal refining components. The current embodiment of the signal refining components and logic circuit are illustrated in more detail in FIG. 23B. The circuit diagram shows the use various logic level field effect transistors used in combination with an Arduino circuit board to control waveform frequency. The signal refining components are used to step down the voltages and currents to physiologically appropriate levels.

The alpha-prototype was programmed to create a biphasic balanced pulse at a frequency of 1 Hz, as illustrated in FIG. 24. It can be seen this waveform is representative of one embodiment of the modulation waveforms mentioned above. It will be obvious to those skilled in the field that these circuits represent a single embodiment capable of generating the desired waveform. Utilization of various circuitry components, logic gates, power sources, and programming can be combined to create the desired waveforms described in the technical description across all possible frequency and amplitude ranges.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for neutralizing pain-inducing components in a nociceptive signal in an afferent pathway, the method comprising:
A) acquiring a nociceptive signal at a sensing point in an afferent pathway, the nociceptive signal having a temporal profile;
B) performing a time domain to frequency domain transformation of the temporal profile to create a first frequency based power analysis identifying corresponding frequency components of the nociceptive signal acquired;
C) comparing the first frequency based power analysis with a second frequency based power analysis of a comparison control signal having a temporal profile;
D) identifying at least one frequency component not present in the first frequency based power analysis that is present in the second frequency based power analysis; and E) generating a correction signal which when combined with the nociceptive signal results in a modified nociceptive signal having a temporal profile similar to the temporal profile of the comparison control signal.

2. The method of claim 1 wherein the nociceptive signal acquired is perceived as pain by a mammalian subject.

3. The method of claim 2 wherein the modified nociceptive signal is perceived as less pain by a mammalian subject than the nociceptive signal acquired.

4. The method of claim 1 further comprising:
F) applying a modulation signal to the afferent pathway distal of the sensing point in the afferent pathway.

5. The method of claim 1 wherein E) comprises:
E1) generating a modulation signal which when applied to the afferent pathway causes the at least one frequency component not present in the first frequency based power analysis to be at least partially present in a nociceptive signal distal of the sensing point.

6. The method of claim 5 wherein E) comprises:
E2) applying the modulation signal to the afferent pathway distal of the sensing point.

7. The method of claim 1 wherein D) comprises:
D1) identifying plural frequency components not present in the first frequency based power analysis that are present in the second frequency based power analysis.

8. The method of claim 7 wherein E) comprises:
E1) generating a modulation signal which when applied to the afferent pathway causes at least one of the plural frequency components not present in the first frequency based power analysis to be at least partially present in a signal in the afferent pathway distal of the sensing point.

9. The method of claim 8 wherein E) comprises:
E2) applying the modulation signal to the afferent pathway distal of the sensing point.

10. The method of claim 7 wherein E) comprises:
E1) generating a modulation signal which when applied to the afferent pathway causes the plural frequency components not present in the first frequency based power analysis to be at least partially present in a signal in the afferent pathway distal of the sensing point.

11. The method of claim 10 wherein E) comprises:
E2) applying the modulation signal to the afferent pathway distal of the sensing point.

12. An electromagnetic stimulation system comprising:
memory for storing a plurality of temporal profiles of pain signals;
an input section receptive to a signal acquired at a sensing point in an afferent pathway of a subject, the signal acquired having a temporal profile;
an output unit for connection to at least one electrode; and
a processing module configured to:
compare and determine when a match exists between a temporal profile of the signal acquired and one of the plurality of temporal profiles of pain signals in memory;
perform a time domain to frequency domain transformation of a temporal profile of a pain signal matching the signal acquired to create a first frequency based power analysis identifying corresponding frequency components of the signal acquired;
compare the first frequency based power analysis with a second frequency based power analysis of a comparison signal having a temporal profile;
identify at least one frequency component not present in the first frequency based power analysis that is present in the second first frequency based power analysis;

generate a modulation signal which when combined with the signal acquired at the sensing point results in a modified signal having a temporal profile similar to the temporal profile of the comparison signal.

13. The system of claim 12 wherein the signal acquired is perceived as pain by a mammalian subject.

14. The system of claim 12 wherein the modified signal is perceived as less pain by a mammalian subject than the signal acquired.

15. The system of claim 12 wherein the plurality of temporal profiles of pain signals stored in memory comprise temporal profiles of any of nociceptive pain, inflammatory pain, and neuropathic pain.

16. The system of claim 12 wherein the processing module is configured to generate a modulation signal which when applied to the afferent pathway causes the at least one frequency component not present in the first frequency based power analysis to be at least partially present in a signal in the afferent pathway distal of the sensing point.

17. The system of claim 16 wherein the processing module is configured to apply the modulation signal to the afferent pathway distal of the sensing point.

18. The system of claim 12 wherein the processing module is configured to identify plural frequency components not present in the first frequency based power analysis that are present in the second frequency based power analysis.

19. The system of claim 18 wherein the processing module is configured to generate a modulation signal which when applied to the afferent pathway causes at least one of the plural frequency components not present in the first frequency based power analysis to be at least partially present in a signal in the afferent pathway distal of the sensing point.

20. The system of claim 19 wherein the processing module is configured to apply the modulation signal to the afferent pathway distal of the sensing point.

21. The system of claim 18 wherein the processing module is configured to generate a modulation signal which when applied to the afferent pathway causes the plural frequency components not present in the first frequency based power analysis to be at least partially present in a signal in the afferent pathway distal of the sensing point.

22. The system of claim 21 wherein the processing module is configured to apply the modulation signal to the afferent pathway distal of the sensing point.

* * * * *